(12) United States Patent
Romette et al.

(10) Patent No.: US 7,459,297 B2
(45) Date of Patent: Dec. 2, 2008

(54) ACTIVE TRUNCATED FORM OF THE RNA POLYMERASE OF FLAVIVIRUS

(75) Inventors: Jean-Louis Romette, Marseilles (FR); Bruno Canard, Cassis (FR); Marie-Pierre Egloff, Marseilles (FR); Barbara Selisko, Marseilles (FR); Delphine Benarroch, Marseilles (FR)

(73) Assignee: Centre National de la Recherche Scientifique -CNRS, Paris (FR)

( * ) Notice: Subject to any disclaimer, the term of this patent is extended or adjusted under 35 U.S.C. 154(b) by 428 days.

(21) Appl. No.: 10/857,244

(22) Filed: May 28, 2004

(65) Prior Publication Data

US 2005/0048472 A1 Mar. 3, 2005

Related U.S. Application Data

(60) Provisional application No. 60/474,670, filed on May 30, 2003.

(51) Int. Cl.
*C12N 9/12* (2006.01)
(52) U.S. Cl. .......................................... 435/194; 435/5
(58) Field of Classification Search .............. 424/199.1, 424/186.1, 218.1; 435/5, 91.1, 91.2, 235.1, 435/92.2
See application file for complete search history.

(56) References Cited

FOREIGN PATENT DOCUMENTS

FR 2654113 A1 * 5/1991
WO WO01/60847 * 8/2001

OTHER PUBLICATIONS

See Score sequence search result 14.rag (search done Jun. 1, 2006).*
Bartholomeusz et al., "Synthesis of dengue virus RNA in vitro: initiation and the involvement of proteins NS3 and NS5," Arch Virol, 128, pp. 111-121 (1993).*
Tan et al (Virology 216:317-325, 1996).*
Johansen et al (Journal of General Virology 82:735-745, 2001).*
Vasudevan et al (II Farmaco 56:33-36, 2001).*
Brooks et al., "The interdomain region of dengue NS5 protein that binds to the viral helicase NS3 contains independently functional importin beta 1 and importin alpha/beta-recognized nuclear localization signals," The journal of Biological Chemistry, vol. 277, No. 39 (2002), 36399-36407.*
Johansson et al., "A small region of the dengue virus-encoded RNA-dependent RNA polymerase, NS5, confers interaction with both the nuclear transport receptor importin- and the viral helicase, NS3," Journal of General Virology, 82: 735-45 (2001).*
Yaegashi et al., "Partial sequence analysis of cloned dengue virus type 2 genome," Gene, 46: 257-267 (1986).*
Result 8, .rpr, 2006.*
Sequence search result 3 from .rag, 2006.*
Sequence search results 1-5 from .rpr; search results 1-60 from.rup, 2006.*

* cited by examiner

*Primary Examiner*—Mary E Mosher
(74) *Attorney, Agent, or Firm*—Oblon, Spivak, McClelland, Maier & Neustadt, P.C.

(57) ABSTRACT

The isolation and purification of two domains from a from a flavivirus is provided. Each domain can function independently. Moreover, one domain codes for a sequence that provide polymerase activity. A process for screening possible modulators of the polymerase activity of an isolated and purified polypeptide from flavivirus is also disclosed.

5 Claims, 9 Drawing Sheets

FIG. 1A

```
                    A1              A2              B1      A3                  αx
              .    10        20        30        40        50        60
Seq.ID.  1 Dengue2            .GTGNIGETLGEKWKSRLNALGKSEFQIYKKSGIQEVDRTLAKEGIKRG.ETDHHAVSRGSAKLRWFVERN
Seq.ID.  2 Dengue3            .GTGSQGETLGEKWKKKLNQLSRKEFDLYKKSGITEVDRTEAKEGLKRG.EITHHAVSRGSAKLQWFVERN
Seq.ID.  3 Dengue1            .GTGAQGETLGEKWKRQLNQLSKSENTYKRSGIMEVDRSEAKEGLKRG.ETTKHAVSRGTAKLRWFVERN
Seq.ID.  4 Dengue4            .GTGTTGETLGEKWKRQINSLDRKEFEEYKRSGILEVDRTEAKSALKDG.SKIKHAVSRGSSKIRWIVERG
Seq.ID.  5 WestNile            ..GGAKGRTLGEVWKERLNQMTKEEFTRYRKEAIIEVDRSAAKHARKEGNVTGGHSVSRGTAKLRWLVERR
Seq.ID.  6 Kunjin              ..GGAKGRTLGEVWKERLNQMTKEEFIRYRKEAITEVDRSAAKHARKERNITGGHPVSRGTAKLRWLVERR
Seq.ID.  7 JapaneseEncephalitis ..GRPGGRTLGEQWKEKLNAMSREEFFKYRREAIIEVDRTEARRARRENNIVGGHPVSRGTAKLRWLVEKG
Seq.ID.  8 YellowFever         .GTANGKTLGEVWKEVWKRELNLLDKQQELYKRTDIVEVDRDTARRHLAEGKVDTGVAVSRGTAKLRWFHERG
Seq.ID.  9 Banzi               ..GGSSALTYGEVWKRQLNLLGKQEMNYKVSDILEVDRSHAREVLNSGNDAVGVAVSRGSSKLNWLIERG
Seq.ID. 10 Langat              ..GGSEGDTLGDMWKARLNSCTKEEFAYRRAGVMETDREKARELLKRGETNMGLAVSRGTSKLAWMEERG
Seq.ID. 11 Powassan            ..GGAEGSTLGDIWKRQRLENSCTKEEFAYRRTGVMETNRDQARELLRRGETNMGLAVSRGCAKLAWLEERG
Seq.ID. 12 Tick-borneEncephalitis .GGSEGDTLGDLWKRRLENGCTKEEFAYRRTGILETERDKARELLRRGETNMGLAVSRGTAKLAWLEERG
Seq.ID. 13 LoupingIll          ..GGSDGDTLGDLWKRRENNCTKEEFVYRRTGILETERDKARELLRRGETNMGLAVSRGTAKLAWLEERG
Seq.ID. 14 Modoc               RGICSSAPTLGEIWKRKLNQLDAKEFMAYRRRFVVEVDRNEAREALAKGKTNTGHAVSRGTAKLAWIDERG
Seq.ID. 15 RioBravo            RGVSSSYITYGEQWKRELNKLNAQAFLYKSRLVHEIDRAEAVSNLSKGRTNTGHAVSRGTSKLAWMHERG β1              αA              β2              β3
              70        80        90        100       110       120       130
Seq.ID.  1 Dengue2            MVTPEGKVVDLGCGRGGWSYYCGGLKNVREVKGLTKG.GPGHEEPIPMSTYGWNLVRLQSGVDVFFTPPEK
Seq.ID.  2 Dengue3            MVIPEGRVIDLGCGRGGWSYYCAGLKKVTEVKGYTKG.GPGHEEPVPMSTYGWNIVKLMSGKDVFYLPPEK
Seq.ID.  3 Dengue1            LVKPEGKVIDLGCGRGGWSYYCAGLKKVTEVKGYTKG.GPGHEEPIPMATYGWNLVKLHSGKDVFFTPPEK
Seq.ID.  4 Dengue4            MVKPKGKVVDLGCGRGGWSYYMATLKNVTEVKGYTKG.GPGHEEPIPMATYGWNLVKLHSGVDVFYKPTEQ
Seq.ID.  5 WestNile            FLEPVGKVIDLGCGRGGWCYYMATQKRVQEVRGYTKG.GPGHEEPQLVQSYGWNIVTMKSGVDVFYRPSEC
Seq.ID.  6 Kunjin              FLEPVGKVIDLGCGRGGWCYYMATQKRVQEVRGYTKG.GPGHEEPQLVQSYGWNIVTMKSGVDVFYRPSEC
Seq.ID.  7 JapaneseEncephalitis FVSPIGKVIDLGCGRGGWSYYAATLKKVQEVRGYTKG.GACHEEPMLMQSYGWNLVSLKSGVDVFYKPSEP
Seq.ID.  8 YellowFever         YVKLEGRVIDLGCGRGGWSYYAAAQKEVSGVKGFTLG.RDGHEKPMNVQSLGWNIITFKDKTDIHRLEPVK
Seq.ID.  9 Banzi               YLRPTGRVVDLGCGRGGWSYYTCAAERQVTSVKAYTLG.KEGHEKPRLIQSLGWNIIKFKDKSDITRMTPHA
Seq.ID. 10 Langat              YVTLKGEVVDLGCGRGGWSYYAASRPAVMSVRAYTIG.GKGHESPRMVTSLGWNLIKFRAGMDVFSMEPHR
Seq.ID. 11 Powassan            YATLKGEVVDLGCGRGGWSYYAASRPSVMAVRAYTIG.GKGHETPKMVTSLGWNLIKFRSGMDVFSMATTR
Seq.ID. 12 Tick-borneEncephalitis YATLKGEVVDLGCGRGGWSYYAASRPAVMSVRAYTIG.GKGHEVPKMVTSLGWNLIKFRAGVDVFSMQPHR
Seq.ID. 13 LoupingIll          YRTLKGEVVDLGCGRGGWSYYAASQPNVREVKAYTLG.GRGHEVPKMVTSLGWNLIRFRSGMDVFSMQPHR
Seq.ID. 14 Modoc               GVELKGSVVDLGCGRGGWSYYAAAQERVRKVNAYTLG.TSGHEKPRLVETFGWNLITFKSKVDVRKMEPFQ
Seq.ID. 15 RioBravo            YVPLKGVVVDLGSGRGGWSYYAAAQERVRKVNAYTLATTKGHEQPRLVQSYGWNLVTFK.KADVRTIEPYP
```

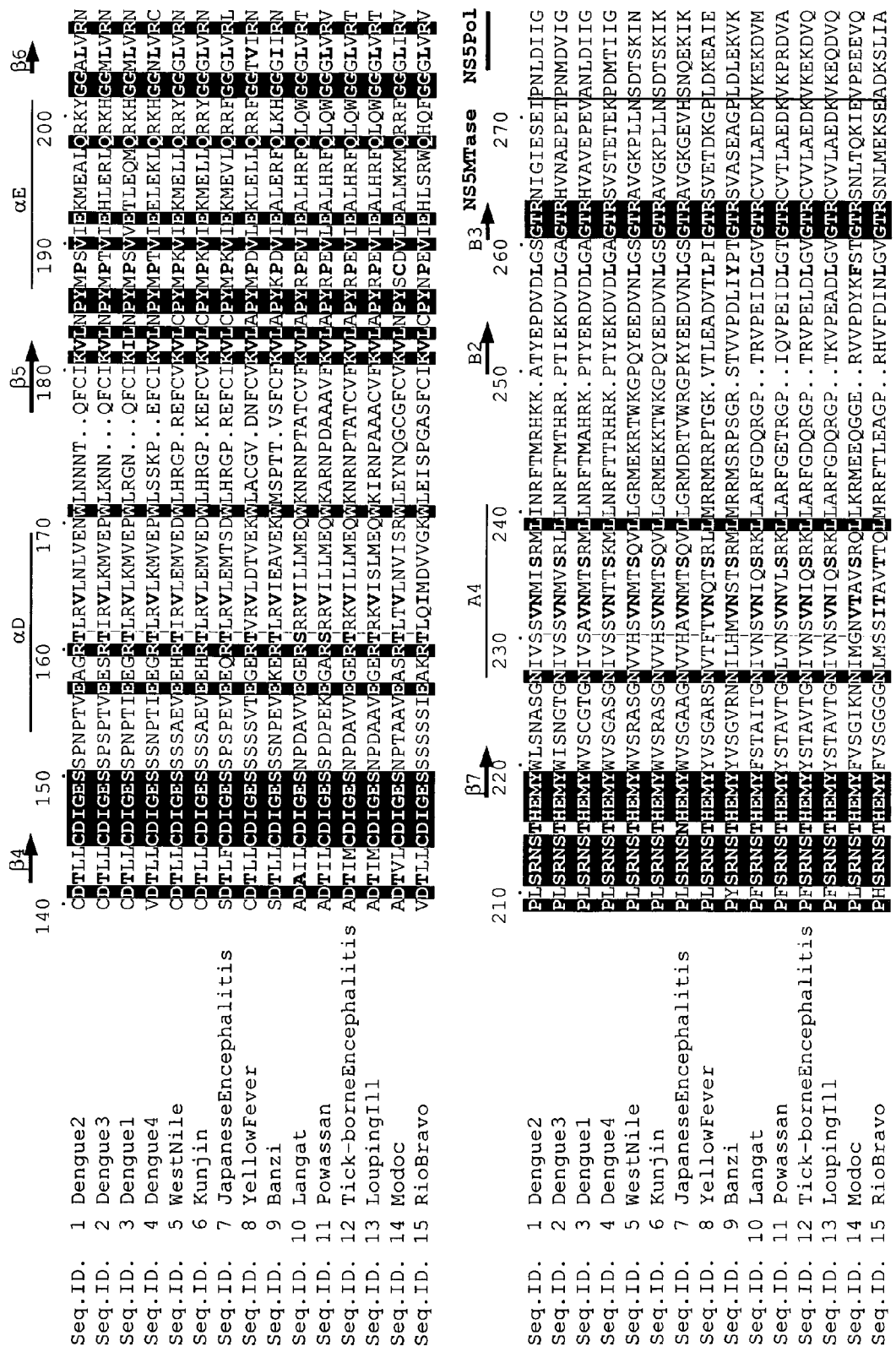

FIG. 1C

```
         280       290       300       310       320       330       340
Seq.ID.  1 Dengue2            KRIEKIKQEHETSWHYDQDHPYKTWAYHGSYETKQTGSASSMGNGVVRLLTKPWDVVPMVTQMAMTDTTPF
Seq.ID.  2 Dengue3            ERIKRIKEEHSSTWHYDDENPYKTWAYHGSYEVKATGSASSMINGVVKLLTKPWDVVPMVTQMAMTDTTPF
Seq.ID.  3 Dengue1            QRIENIKNEHKSTWHYDEDNPYKTWAYHGSYEVKPSGSASSMVNGVVRLLTKPWDVIPMVTQIAMTDTTPF
Seq.ID.  4 Dengue4            RRLQRLQEEHKETWHYDQENPYRTWAYHGSYEAPSTGSASSMVNGVVKLLTKPWDVIPMVTQLAMTDTTPF
Seq.ID.  5 WestNile            NRIERLRREYSSTWHHDENHPYRTWNYHGSYDVKPTGSASSLVNGVVRLLSKPWDTITNVTTMAMTDTTPF
Seq.ID.  6 Kunjin              NRIERLRREYSSTWHHDENHPYRTWNYHGSYEVKPTGSASSLVNGVVRLLSKPWDTITNVTTMAMTDTTPF
Seq.ID.  7 JapaneseEncephalitis KRIQKLKEEFATTWHKDPEHPYRTWTYHGSYEVKATGSAASSLVNGVVKLMSKPWDAIANVTTRMAMTDTTPF
Seq.ID.  8 YellowFever         ERVERIKSEYMTSWFYDNDNPYRTWHYHYCGSYVTKTSGSAAASMVNGVIKILTYPWDKIEEVTNMAMTDTTPF
Seq.ID.  9 Banzi               ARINRLKEEQESTWFVDSDHPYRTWQYHGSYKTAATGSSAASLLNGVVKLLSWPWNAREDVVRMAMTDTTAF
Seq.ID. 10 Langat              ERIQALKDQYCDTWHEDHEHPYRTWQYWGSYRTPATGSAAASLINGVVKLLSWPWNAREDVTRMAMTDTTAF
Seq.ID. 11 Powassan            ERIGALREQYSESWHEDKEHPYRTWQYWGSYRTAPTGSAAPTGSAASLINGVVKLLSWPWNAREDVVRMAMTDTTAF
Seq.ID. 12 Tick-borneEncephalitis ERISALREQYGETWHMDREHPYRTWQYWGTSRTAPTGSAASLINGVVKLLSWPWNAREDVVRMAMTDTTAF
Seq.ID. 13 LoupingIll          ERIRALRKQYSETWHMDEEHPYRTWQYWGTSRTAPTGSAAALINGVVKLLSWPWNAREDVVRMAMTDTTAF
Seq.ID. 14 Modoc               MRVDKIKAEKSGTWCFDSNHPYRTWNYHGSYRVRDVGTRASAVNHVVKLLSWPWGKMEKVLAMSMTDTTAF
Seq.ID. 15 RioBravo            DRITIIQNENKASWHQDPNQPYRTWTYHGSYSIRDVGTSASAPNHVVKLLAWPWLKIEKVVLMAMTDTTAF
```

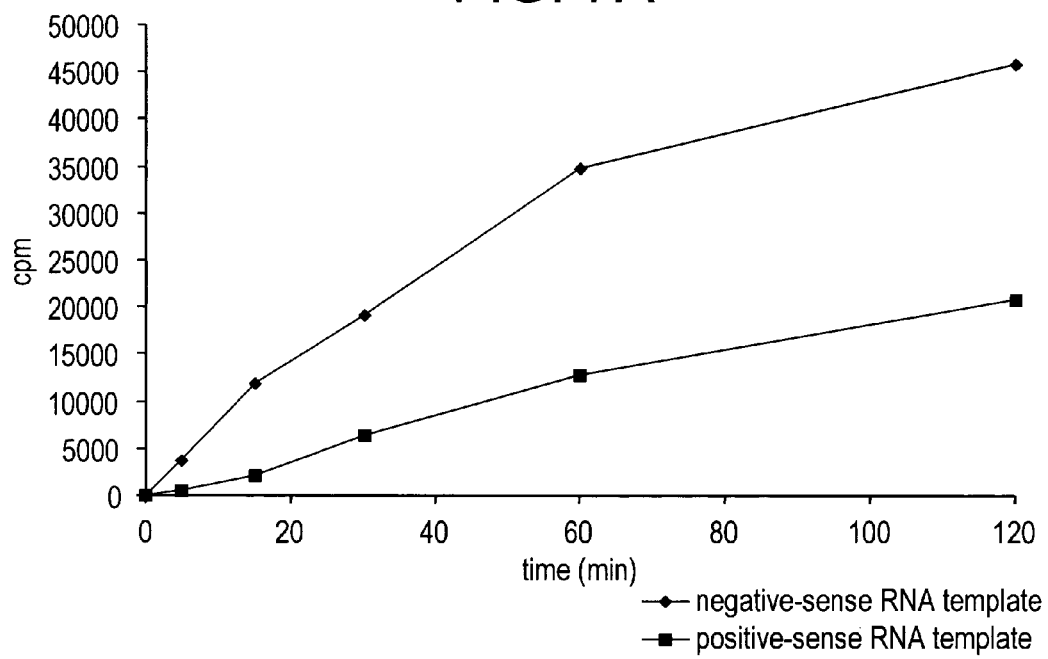
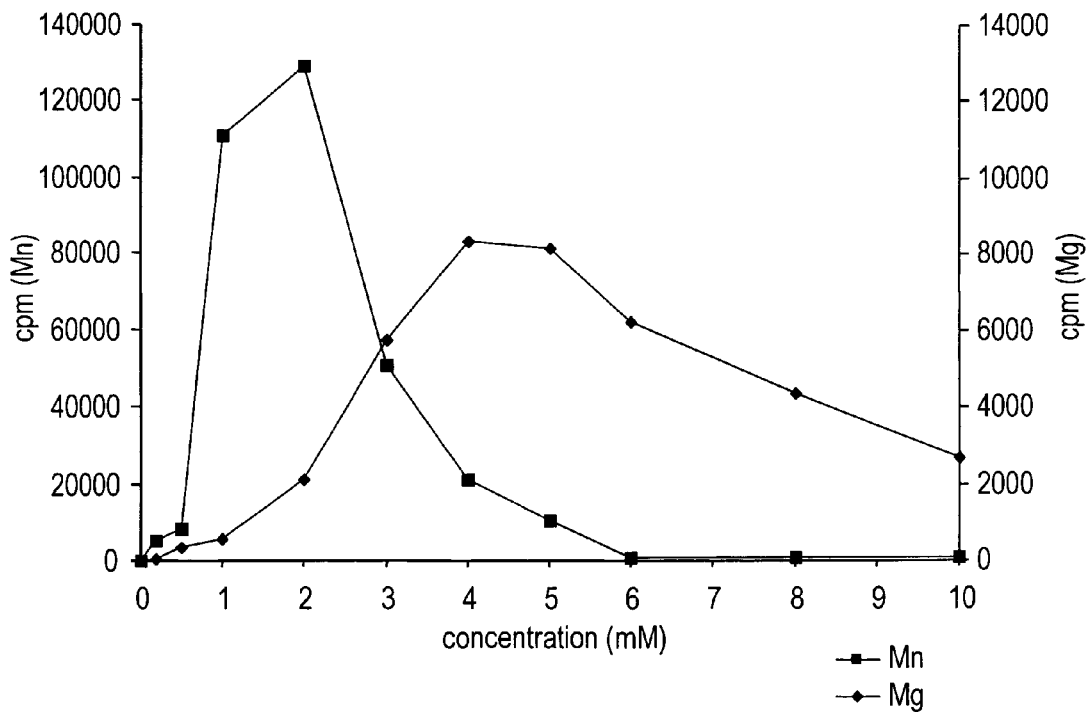

US 7,459,297 B2

ACTIVE TRUNCATED FORM OF THE RNA POLYMERASE OF FLAVIVIRUS

CROSS REFERENCE TO RELATED APPLICATION

This application claims the benefit of U.S. Provisional Application No. 60/474,670, filed May 30, 2003, the subject matter of which is fully incorporated herein by reference.

FIELD OF INVENTION

This invention relates to antiviral molecular biology. More particularly, it relates to the isolation and identification of an active truncated form of the RNA polymerase of flavivirus, capable of being easily reproduced, and serving as a target for high-throughput screening of antiviral drugs.

BACKGROUND

The genus flavivirus contains approximately 70 positive single-stranded RNA viruses, among which many major human pathogens are found, including Dengue virus ("DV"), West Nile ("WNV"), Yellow Fever virus ("YFV"), Japanese and tick-borne encephalitis viruses. YFV was the first flavivirus to be isolated in 1927, but historically, flavivirus-like diseases have been reported in the medical literature since at least 1780.

On of the most common and virulent flaviviruses is DV. DV threatens up to 2.5 billion people in 100 endemic countries. Up to 50 million infections occur annually with 500 000 cases of dengue haemorrhagic fever and 22,000 deaths mainly among children. Dengue has been classified by the World Health Organization ("WHO") as a priority as it ranks as the most important mosquito-borne viral disease in the world. In the last 50 years, its incidence has increased 30-fold. Prior to 1970, only 9 countries had experienced cases of dengue haemorrhagic fever ("DHF"); since then the number has increased more than 4-fold and continues to rise.

WNV also has become much more wide-spread. In 1999, WNV was isolated for the first time in the Americas during an outbreak in New York City. By the end of 2002, WNV activity had been identified in 44 states of the United States and the District of Columbia. The 2002 WNV epidemic resulted in 4,156 reported human cases of WN disease including 2,942 meningoencephalitis cases and 284 deaths.

There have been previous attempts to generate a vaccine. For example, a live, attenuated virus of YFV (strain 17D) was developed in 1936 and has been used as a vaccine for over 400 million people. Unfortunately, the vaccine has not proved 100% successful since there are 200,000 estimated cases of yellow fever (with 30,000 deaths) per year worldwide, 90% of which in Africa. Chimeric live vaccines incorporating genes of either Japanese encephalitis, WNV, or Dengue in a YFV 17D vector are currently in development. However, a number of difficulties are associated with the conception of safe and efficient vaccines, such as vaccine purity, and immunogenic cross responses. That is why antiviral chemotherapy has a major role to play in the control of such diseases.

Since viral RNA polymerase is critical for replication of the virus and cannot be substituted by any other cellular polymerase, it is an excellent antiviral target. As a result, most of the more than 30 new antiviral agents, which have been developed and approved during the last 5 years, are directed against viral polymerases. They are mainly targeted against human immuno-deficiency virus, but drugs against hepatitis B and C, herpes simplex, varicella-zoster and influenza virus infections have also been made commercially available.

More than 50% of these antiviral agents are nucleoside analogues, in which the base, the ribose moiety or both have been modified. Nucleoside analogues can act as inhibitory ligands by binding to the template binding site within the polymerase active site and preventing the access of the viral RNA, or by binding to the nucleotide binding site, thus limiting the availability of the natural substrate for complementary strand synthesis. It is generally understood in the art that a nucleoside analogue may be a synthetic molecule that resembles a naturally occurring nucleoside, but lacks a bond site needed to link it to an adjacent nucleotide. Additionally, nucleoside analogues can also act as chain-terminators during DNA or RNA synthesis, by binding themselves as a substrate for the target polymerase, but preventing further chain elongation. Non-nucleoside analogues may bind to allosteric sites thus influencing the local conformation of the active site via long-range conformational changes of the polymerase's structure.

Another approach whereby many antiviral compounds have been discovered is by using cell cultures infected with the virus of interest. In such cases, addition of an antiviral compound protects the cells from infection, or inhibits virus growth. For this type of experiment, it is useful to identify a large number of antiviral compounds in an efficient manner. As such, another evolving mechanism to identify new antiviral agents through the high-throughput screening ("HTS") of a large number of synthetic or natural compounds. This requires the development of an in vitro assay, which in turn requires large amounts of soluble and active protein.

When a high number of potentially antiviral compounds are tested by HTS, it is possible to identify antiviral compounds in an efficient manner. This approach has been used successfully for HIV and other viruses. However, in some cases, this approach is difficult due to the absence of a suitable system allowing infection of a cell in vitro.

In other cases, even if a suitable cell-based assay is available, this procedure may be too cumbersome or expensive. This is the case for certain dangerous viruses—such as those that require BSL-3 and/or BSL-4 facilities. Establishing a screening process for over a large amount of compounds in a BSL-3 or BSL-4 containment facility has not been achieved yet because of this heavy expense and burden. For example, flaviviruses belong to this class of viruses. These viruses require from BSL-2 to BSL-4 facilities (e.g., Dengue, WNV and/or Kyasanur Forest viruses). Thus, in such cases, it is preferable to screen potentially antiviral compounds directly on viral target proteins.

For efficiency, especially considering the difficulty with certain, more dangerous viruses, the characterization in molecular terms of the target, the viral polymerase, is of prime importance in the screening and selection of antiviral compounds. In the case of the flavivirus RNA polymerase ("NS5" or sometimes referred to herein as "NS5Pol"), this task has proven to be difficult for several reasons. First, polymerase genes have been notoriously difficult to clone in their entirety. When available, recombinant NS5 has been reported to be unstable in bacterial hosts. In addition, the notoriously low yield of soluble purified NS5 is a limiting factor to set up polymerase-activity assays. Another possible reason for the described difficulties is the fact that NS5 does not carry a single enzymatic activity.

Very recently, we described an N-terminal domain of NS5 (sometimes referred to herein as "NS5 methyltransferase domain") which acts as an S-adenosyl-L-methionine (AdoMet)-utilizing RNA-cap 2'Omethyltransferase, thus participating in mRNA capping, which is generally understood as the process of adding a guanosine nucleotide to the 5' end of mRNA (the methelyated end of guanosine) (Egloff & Benarroch, 2002). Additionally, we showed that the NS5 methyltransferase domain binds GTP analogues.

Due to the nature and proximity of the NS5 methyltransferase domain to the polymerase domain of the flavivirus, the description and characterization of the NS5 methyltransferase domain clearly shows that some nucleoside analogues and inhibitors of flavivirus replication could potentially be, in fact, mRNA-capping inhibitors without any effect on the polymerase activity. Likewise, it is very possible to mistakenly identify a compound as binding to NS5 and characterizing the binding data as potentially interesting for inhibition of the polymerase, but, in reality, only the RNA-capping has been affected. Therefore, it would be useful to identify and define the "junction" or sequence between the NS5 methyltransferase domain and the polymerase domain.

SUMMARY OF THE INVENTION

This invention relates to the isolation and purification of a polypeptide from a flavivirus.

In another aspect of the invention, the polypeptide can be separated into two domains, the N-terminal domain and the C-terminal domain, both of which are separately active.

In another aspect of the invention, the junction between the N-terminal and C-terminal domains has been identified.

In yet another aspect of the invention, the results indicated that independent expression of each of the separated domains provided greater expression than the full, unseparated polypeptide.

In still another aspect of the invention, the C-terminal of the domains in particular is purified and acts as active RNA polymerase.

In yet another aspect of the invention, the C-terminal domain demonstrates substantial homology with other RNA polymerases of clinical interest.

In still another aspect of this invention, the polymerase provides a surrogate model and system to screen synthetic and natural compounds against the polymerases of related viruses.

BRIEF DESCRIPTION OF THE FIGURES

FIG. 1 shows the sequence alignment of NS5 of flaviviruses: Dengue2 (SEQ ID NO. 1); Dengue3 (SEQ ID NO. 2); Dengue1 (SEQ ID NO. 3); Dengue4 (SEQ ID NO. 4); West-Nile (SEQ ID NO. 5); Kunjin (SEQ ID NO. 6); JapaneseEncephalitis (SEQ ID NO. 7); YellowFever (SEQ ID NO. 8); Banzi (SEQ ID NO. 9); Langat (SEQ ID NO. 10); Powassan (SEQ ID NO. 11); Tick-borneEncephalitis (SEQ ID NO. 12); LoupingIll (SEQ ID NO. 13); Modoc (SEQ ID NO. 14); RioBravo (SEQ ID NO. 15).

FIG. 7 shows two graphs demonstrating the activity level of NS5PolDV on specific heteropolymeric RNA templates.

DETAILED DESCRIPTION

Definitions

Figure 2A:
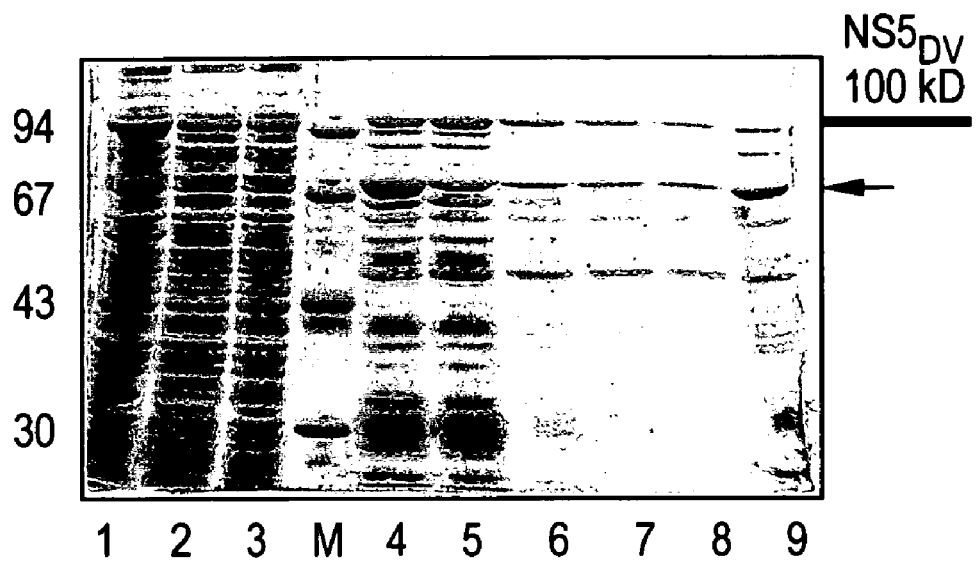
FIG. 2 shows two Western blots illustrating the expression and purification of NS5DV and NS5Pol$_{DV}$.

"Structural equivalents" should be understood to mean a protein maintaining its conformational structure as if the protein were the native protein expressed in its natural cell.

"Substantial homology" or "substantially homologous" means a degree of homology between the isolated and described NS5Pol (as defined herein) and the RNA polymerases of other positive-single-stranded RNA viruses of clinical interest when there is homology at least about 65%, preferably at least about 70%, most preferably in excess of 80%, and even more preferably in excess of 90%, 95% or 99%.

Results and Findings

In one aspect of this invention, we discovered a way to circumvent the above-described problems associated with viral polymerase. We performed a structural analysis of flaviviruses NS5 genes using biocomputing methods, and isolated and defined two unique domains of NS5. As described in the literature, two distinct domains are generally defined for the large family of flavivirus NS5 genes, and related structural equivalents.

Specifically, as shown in the experiments, NS5 was separated into the two domains using genetic engineering techniques. We have established the independent folding of these two putative domains using various methods. Moreover, demonstrated in our experiments as set forth below, each domain is separately active, and an appropriate ligand may be mapped to either the N-terminal (capping) domain or the C-terminal (polymerase) domain of NS5. These genetic constructs allow the production of higher quantities of either domain compared to the full-length protein. Thus, simply put, the C-terminal polymerase domain of NS5 (NS5Pol) of DV (subtype 2, Strain New Guinea C), WNV (strain New York 99) and the Kunjin variant of WVN (KV) are easy to purify in large quantities, they are active as a polymerase, and constitute one aspect of our invention.

As noted, the availability of large quantities of NS5Pol allows its use as a target in HTS. One of the advantages of the isolation of the polymerase domain is that the antiviral compound, which demonstrates the modulating activity of the polymerase domain, is specific to the polymerase activity of the viral protein, without any interference of the other parts of the protein. Indeed, it is possible to detect RNA polymerase activity in a single tube using standard radioactive or nonradioactive methods.

As described herein, modulation of the polymerase activity of the protein is important in creating antiviral agents for the treatment of the enumerated viral diseases. Since DV, WNV and KV NS5Pol domains are significantly homologous to and demonstrate substantial homology with NS5Pol domains of other flaviviruses, and since DV, WNV and KV NS5Pol are functionally homologous to the RNA polymerases of other positive-single-stranded RNA viruses of clinical interest (such as the related NS5B polymerase of HCV), NS5Pol provides also a surrogate model and system to screen synthetic and natural compounds against such related viruses. Simply put, the invention includes a method of screening antiviral compounds able to modulate the polymerase activity of significantly and functionally homologus NS5 gene encoding viruses (i.e. flaviviruses).

Expression and Purification

Based on preceding structural and functional studies on a N-terminal methyltransferase or capping domain of protein NS5 of flavivirus (Egloff and Benarroch, 2002) we predicted the limit of a functional and soluble C-terminal polymerase domain of NS5. In particular, FIG. 1 identifies the sequence alignment of various flaviviruses as follows: Dengue 2 (P14340) (SEQ ID NO. 1), Dengue 3 (Q99D35) (SEQ ID NO. 2), Dengue 1 (Q8VBS3) (SEQ ID NO. 3), Dengue 4 (AAA42964) (SEQ ID NO. 4), West Nile virus (AAL87234) (SEQ ID NO. 5), Japanese encephalitis virus (Q82872) (SEQ ID NO. 7), Yellow fever virus (Q89277) (SEQ ID NO. 8), Banzi virus (Q67483) (SEQ ID NO. 9), Langat virus (Q9IG40) (SEQ ID NO.10), Tick-borne encephalitis virus (Q8VBS4) (SEQ ID NO. 12), Louping ill virus (O10383) (SEQ ID NO. 13), Modoc virus (CAC82912) (SEQ ID NO. 14) and Rio Bravo virus (Q9JAD5) (SEQ ID NO. 15) were aligned by ClustalW. The secondary-structure elements of the NS5MTaseDV structure as determined by X-ray crystallography and of NS5PolDV as predicted by PredictProtein are displayed in black and red, respectively, above the sequence of NS5 Dengue. NS5Pol starts after the vertical bar just before a predicted alpha-helix. The remaining ca. 550 residues of NS5 are not shown.

As set forth above, FIG. 1 shows the sequence alignment of the N-terminal part of NS5 of several flaviviruses with the secondary structure elements of the capping domain of Dengue NS5 given above. Essentially, as discussed, the junction between the methyltransferase and polymerase portion of the flaviviruses was isolated, which allows the precise and efficient separation of the domains. The junction (or where the Pol domain starts) is located at amino acid 272.

Proteins NS5 and their corresponding Pol domains of DV, KV and WNV were expressed as recombinant proteins bearing a His-tag which facilitates subsequent purification. Accordingly, they were purified with immobilized metal-affinity chromatography (IMAC) in a first purification step. As noted above, FIG. 2 illustrates the superiority of NS5PolDV over NS5DV in terms of purification yield after IMAC following the same protocol. The results shown in FIG. 2, the expression and purification of NS5DV and NS5PolDV, were obtained as follows: NS5DV and NS5PolDV were cloned in expression plasmid pQE30, expressed in BL21[pDNAy] overnight at 17° C. after induction with 50 mM IPTG, addition of 2% EtOH and a cold shock (30 min at 4° C.). Sonication was done in 50 mM sodium phosphate lysis buffer, pH 7.5, 300 mM NaCl, 10% glycerol (10 ml of this lysis buffer for 3.6 g cell pellet) in the presence of DNAse, PMSF, protease inhibitors and lysozyme. Recombinant proteins were bound to metal-affinity-chromatography resin talon (Clontech) and eluted with 500 mM imidazole. SDS-PAGE of protein samples from expression and purification: upper panel: NS5DV, lower panel: NS5PolDV, lane 1: total fraction after lysis, lane 2: soluble fraction after lysis and centrifugation, lane 3: flowthrough of metal-affinity column, lane M: molecular mass markers, lanes 4 to 8: eluted fractions from metal-affinity column, F1 to F5, lane 9: metalaffinity resin. The corresponding molecular masses in kD of the markers are given on the left. NS5DV results in low purification yields due to instability resulting in the presence of a protein band the size of which corresponds to the polymerase domain (see arrow in the upper panel).

Figure 2B:
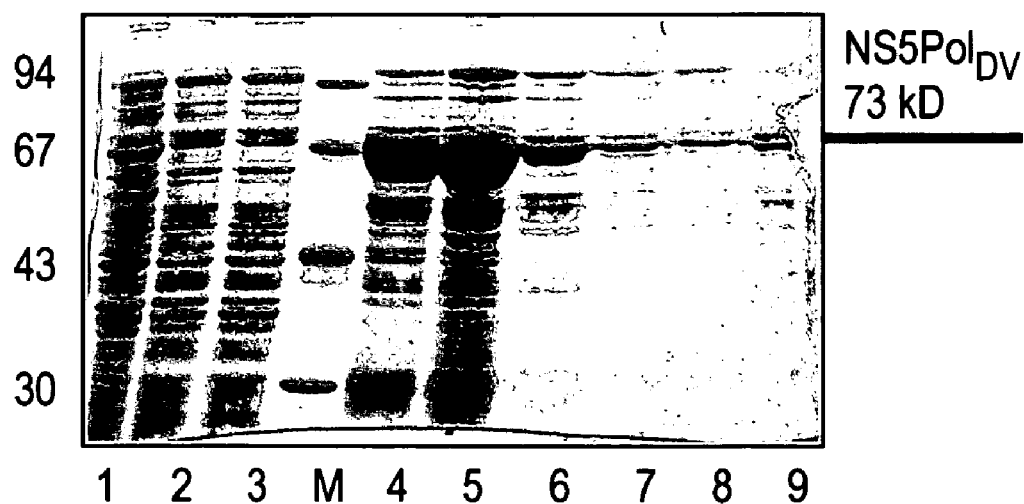

The low yield of NS5 is attributed to lower solubility of the recombinant protein and an elevated sensitivity to proteolytic cleavage during purification. This is illustrated in FIG. 2 by the presence of a cleavage product of around 73 kD which could represent the Pol domain. Yields for both proteins are compared in Table 1.

TABLE 1

| Yield after expression and purification | | |
|---|---|---|
| | Yield (mg per liter expression culture) | |
| protein | after IMAC | after heparin |
| $NS5Pol_{DV}$ | 2 | 1.2 |
| $NS5_{DV}$ | 0.2 | n.d. |
| $NS5Pol_{KV}$ | 10 | 7 |
| $NS5_{KV}$ | 7 | 0.6 |
| $NS5Pol_{WNV}$ | 12 | 8 |
| $NS5_{WNV}$ | n.d. | n.d. |

A second purification step consists of heparin affinity chromatography. The results of this purification were illustrated in FIG. 3 and obtained pursuant to the following procedure: NS5PolDV eluates from metal-affinity chromatography were dialyzed against 50 mM sodium phosphate buffer, pH 7.5, 150 mM NaCl, 10% glycerol and submitted to heparin-affinity chromatography applying a salt gradient of 150 mM to 1M NaCl. Pure protein was eluted in two peaks, at 390 mM and 460 mM NaCl.

A: SDS-PAGE of protein samples from purification steps, lane 1: pooled protein fractions from metal-affinity chromatography after dialysis, lane M: molecular mass markers, lane 2: peak 1 from heparin-affinity chromatography, lane 3: peak 2 from heparin-affinity chromatography, lane 4: flowthrough from heparin-column. The corresponding molecular masses in kD of the markers are given on the left.

B: Analytical gel filtration (Superdex 200, Pharmacia) of peak 1 and 2 of NS5PolDV from heparin affinity chromatography. The elution volume of peak 1 corresponds to the monomeric form of NS5PolDV whereas peak 2 elutes earlier corresponding to oligomeric NS5PolDV (trimer or tetramer).

Figure 3A:
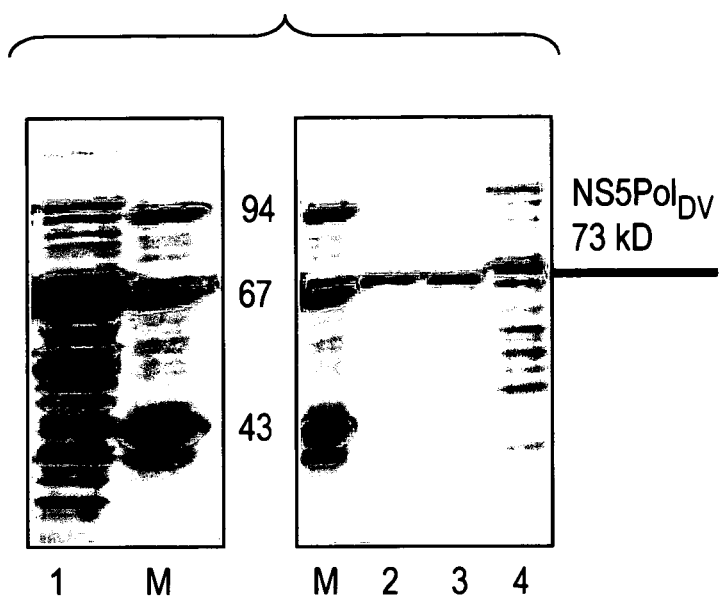
FIG. 3 shows a Western blot (FIG. 3A) and a graph (FIG. 3B) of the purified NS5Pol$_{DV}$.
Figure 3B:
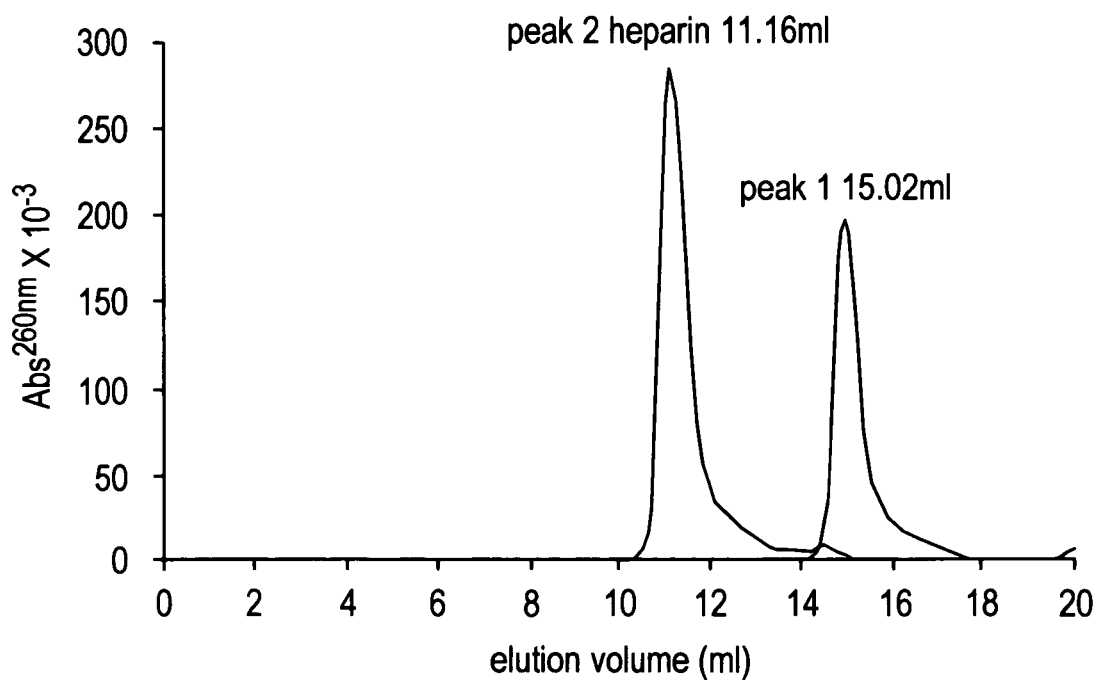

For NS5PolDV it results in two fractions eluting at different salt concentrations both representing NS5PolDV, as shown in FIG. 3A. Analytical gel filtration showed that peak 1 from heparin affinity chromatography represents the monomeric form of NS5PolDV whereas peak 2 represents an oligomeric form as shown in FIG. 3B. Both forms are purified to 98% after heparin purification step, the combined yield of NS5PolDV is 1.2 mg starting from one liter expression culture (Table 1).

Expression and purification of NS5 KV and NS5PolKV follow a similar tendency compared to Dengue NS5 (sequence identity of NS5 66.4%). Although full-length NS5 KV and NS5PolKV render considerably higher yields compared to the corresponding Dengue proteins, still, full-length NS5 KV shows lower yields after one purification step (Table 1) and, due its instability, dramatically lower yields after a second purification step. In difference to NS5PolDV, NS5PolKV elutes as a single peak after heparin affinity chromatography (data not shown). The same applies to NS5PolWNV (sequence identity to NS5PolKV 94.6%).

In all cases, the final purification product, for which the purity is adequate for HTS assays, is purified with a >10-fold increase in yield compared to the unengineered polymerase.

Activity Data

Polymerase activity on NS5Pol was measured on homo- and heteropolymeric templates.

Homopolymeric Template

Activity was tested on three homopolymeric templates: poly(rC), poly(rU) and poly(rA). Only poly(rC) resulted to be a productive template for NS5PolDV. This was illustrated in FIG. 4 based on the following protocol: RNA polymerase activity was tested on a homopolymeric RNA template (polycytidylic acid, Amersham Biosciences) of an average length of 360 nt. A standard assay was carried out in 50 mM HEPES buffer, pH 8.0, 10 mM KCl, 5 mM MgCl2, 5 mM MnCl2, 10 mM DTT containing 1 µM template, 4 mM primer GG, 10 µM GTP, 0.01 mCi [3H]-GTP per µl reaction mixture and the concentration of enzyme given below. Reactions were carried out at 30° C. for given time periods and stopped by spotting a sample on DEAE filter discs (Whatman) presoaked with 50 mM EDTA. Filters were washed 3×10 min with 300 mM (NH4)2SO4 buffer, pH 8.0 and 2×5 min with EtOH and air-dried. Liquid scintillation fluid was added and incorporation in counts per minute (cpm) determined by using a Wallac MicroBeta TriLux Liquid Scintillation Counter.

A: Influence of specific *E. coli* RNA polymerase inhibitor rifampicin on NS5PolDV and *E. coli* polymerase (control). NS5PolDV was tested using the conditions given above at 64-nM enzyme concentration. *E. coli* RNA polymerase was obtained from USBiochemicals and used in NS5PolDV standard rection buffer at 37 nM.

B: Time course of [3H]-GTP incorporation by NS5PolDV peak 1 (monomeric preparation) and peak 2 (oligomeric preparation) from heparin 11 affinity chromatography (see FIG. 3A) tested at 80 nM enzyme concentration using poly (rC) without primer.

Figure 4A:
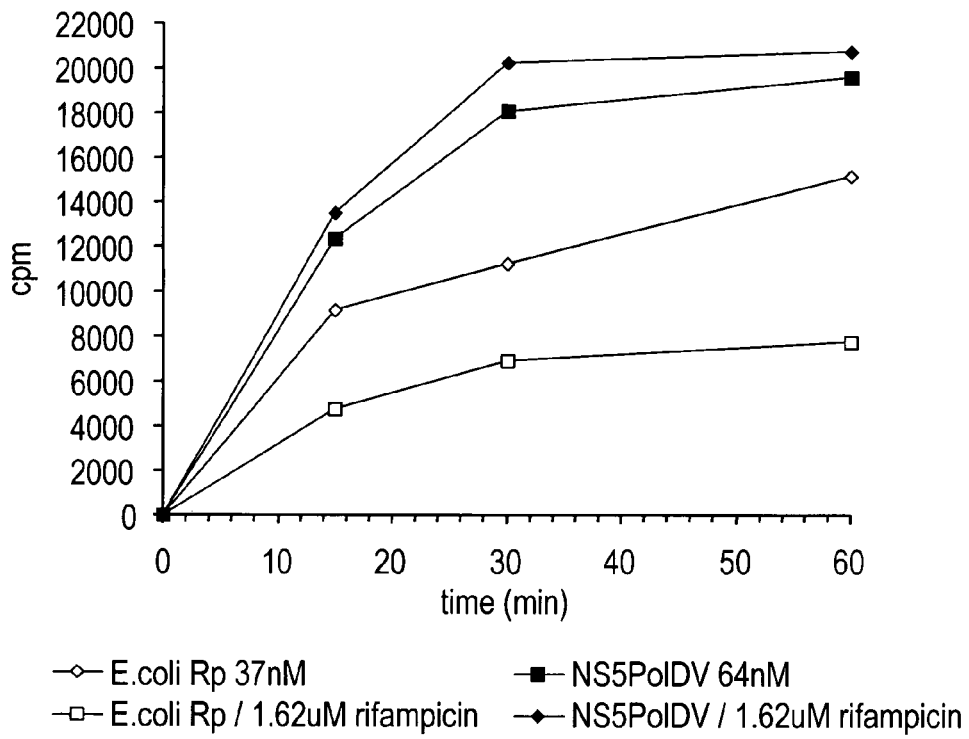
FIG. 4 shows two graphs (FIG. 4A and FIG. 4B) demonstrating the activity level of NS5Pol$_{DV}$ on poly(rC).
Figure 4B:
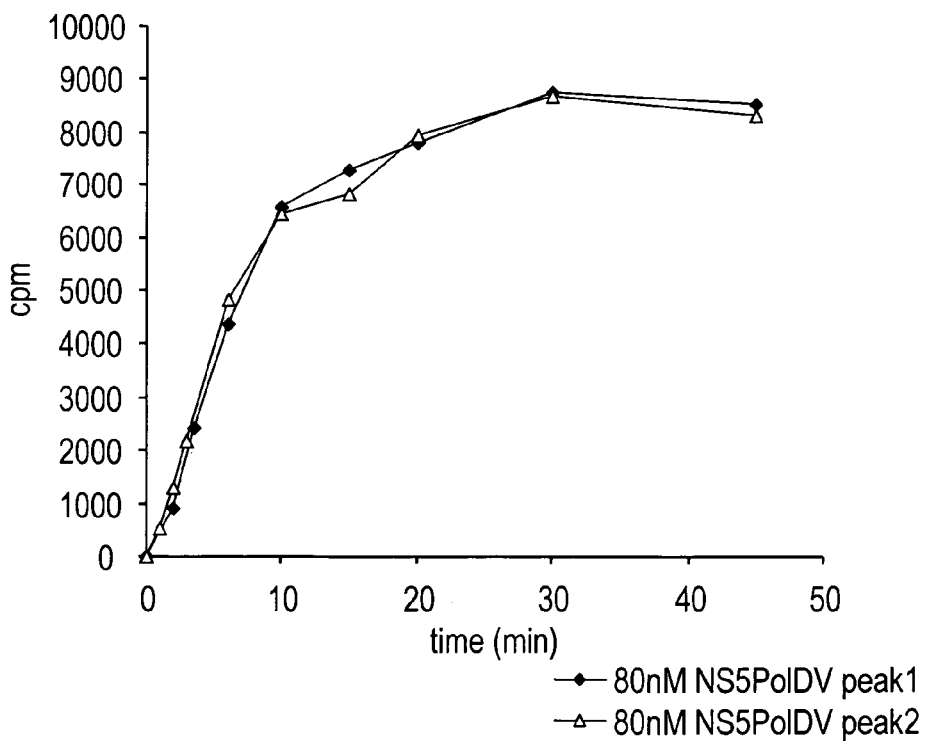

FIG. 4A shows incorporation of radioactively labeled GTP into a nascent poly(rG) polymerization product by NS5PolDV (oligomeric preparation) using primer rGG. In a control reaction *E. coli* RNA polymerase-inhibitor rifampicin was added and did not show any inhibitory effect. Thus, the observed incorporation of radioactive GTP in a polymerization product is not due to a contamination with *E. coli* RNA polymerase activity. FIG. 4B shows a parallel test of the oligomeric and monomeric preparation of NS5PolDV. In this experiment no primer was used, thus, polymerization is initiated de novo. Both preparations show identical catalytic efficiency. There are two possible explanations, either the state of oligomerization does not influence polymerase activity or under the conditions of the activity test (80 nM enzyme 6 concentration) both preparations adopt the same oligomerization state. In either way, both preparations can likewise be used for inhibitor screening studies.

In FIG. 5, the steady-state Km determination of GTP with various ligands was performed as follows: RNA polymerase activity was tested under conditions given in the description set forth above in the experiments related to FIG. 4 without the use of a primer. Initial velocities were determined over a time period of 5 min. GTP concentrations in the range of 2 to 500 µM were tested using poly(rC) at 1 µM. Template poly (rC) was tested in the range of 2 to 1000 nM with GTP fixed at 200 µM.

A: Plot of apparent intitial velocity (viapp in cpm per min) against GTP concentration. Data were fitted to a Michaelis-Menten hyperbola (viapp=Vmax[S]/(Km+[S]) using Kaleidagraph.

B: Plot of apparent initial velocity against poly(rC) concentration. Data were fitted as in A.

Figure 5A:
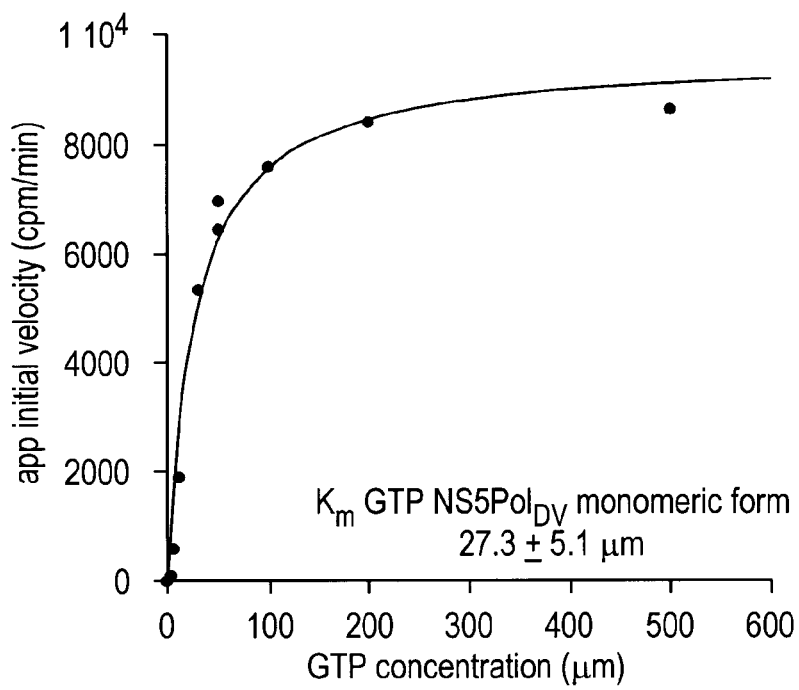
FIG. 5 shows a steady-state Km determination of GTP with and poly(rC) (in FIG. 5A) and for monomeric NS5PolDV using poly(rC) without primer (de novo initiation) (in FIG. 5B).
Figure 5B:
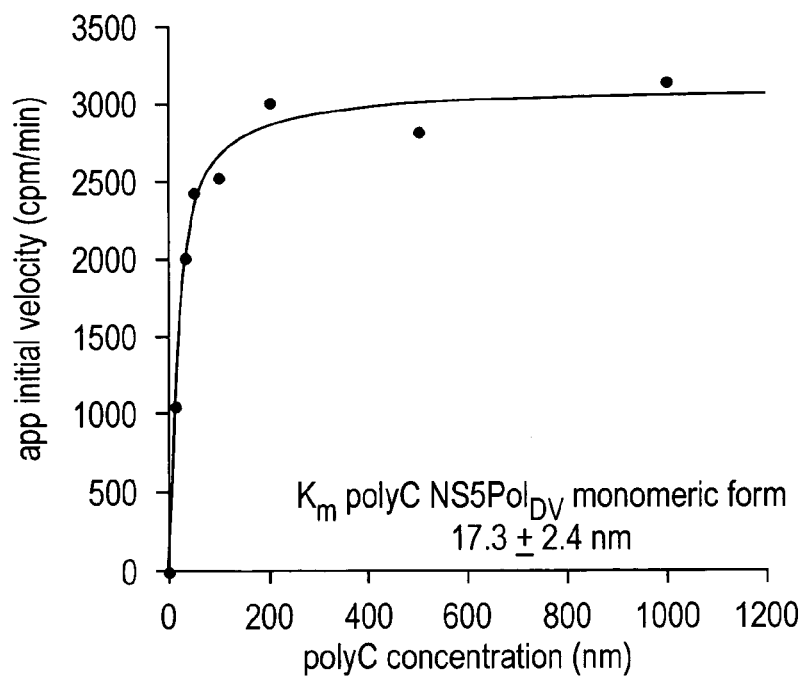

The Km of GTP was determined for NS5PolDV (monomeric preparation) as being 27.3±5.1 mM (FIG. 5A). Km values are in a similar range for the oligomeric preparation of NS5PolDV (66.2±6.6 mM) and for full-length NS5DV (13.0±2.9 mM). Thus, the affinity of NS5PolDV from both preparations versus the substrate GTP that binds to a nucleotide-binding site within the active site of the enzyme are close. This again confirms that both preparations can be used likewise. Additionally, the fact that NS5PolDV shows similar substrate affinity as NS5 indicates that the polymerase domain of flavivirus NS5 is a valid model system for the identification of inhibitors of the full-length protein. The Km values of polyC were determined for the monomeric preparation of NS5PolDV as 17.3±2.4 mM, the oligomeric preparation as 14.8±3.8 mM and for NS5DV as 18.0±7.3 mM. As seen above, the corresponding plot for the monomeric preparation of NS5PolDV is shown in FIG. 5B. First, this allows the conclusion that a putatively different oligomerization status of NS5PolDV does not seem to influence the affinity to a long template which could be expected to maintain cooperative interactions with two enzyme molecules at the same time. Secondly, template poly(rC) (around 360 nt long) shows identical affinity to NS5DV and NS5PolDV within the context of its use as a polymerization template. Thus, the capping domain does not seem to be involved in template binding indicating again that the isolated polymerase domain can be used for inhibitor screening experiments of the polymerase activity of full-length NS5.

Figure 6A:
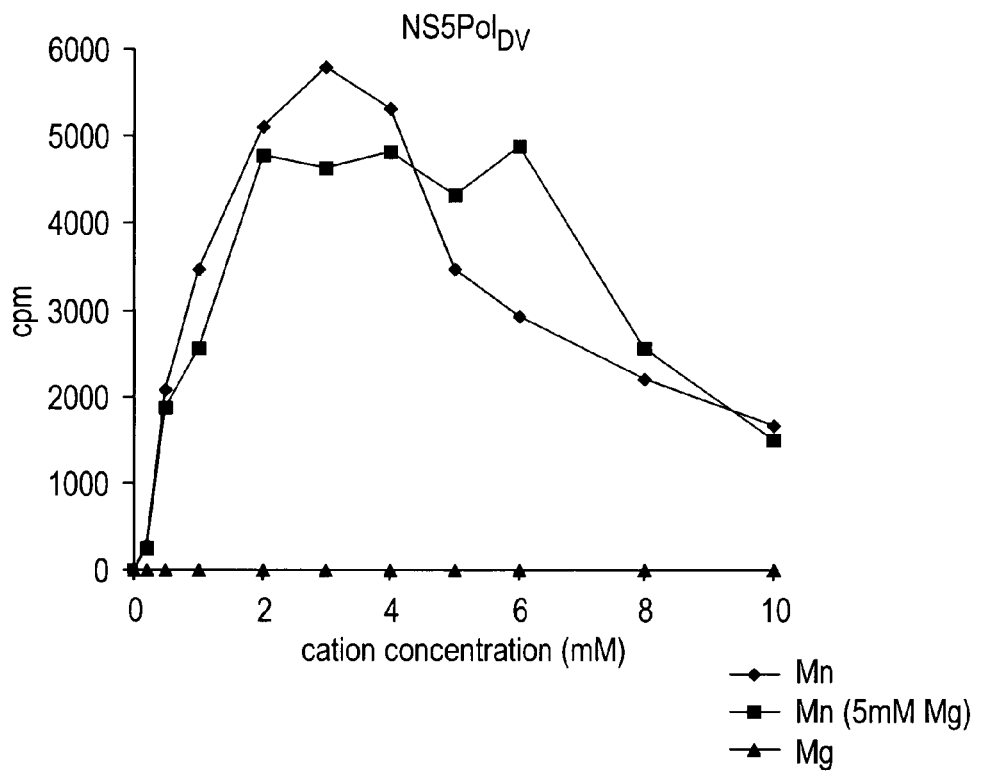
FIG. 6 shows divalent cation optimum curves for NS5PolDV and NS5PolWNV (in FIG. 6A) on poly(rC) without primer (de novo initiation) (in FIG. 6B).
Figure 6B:
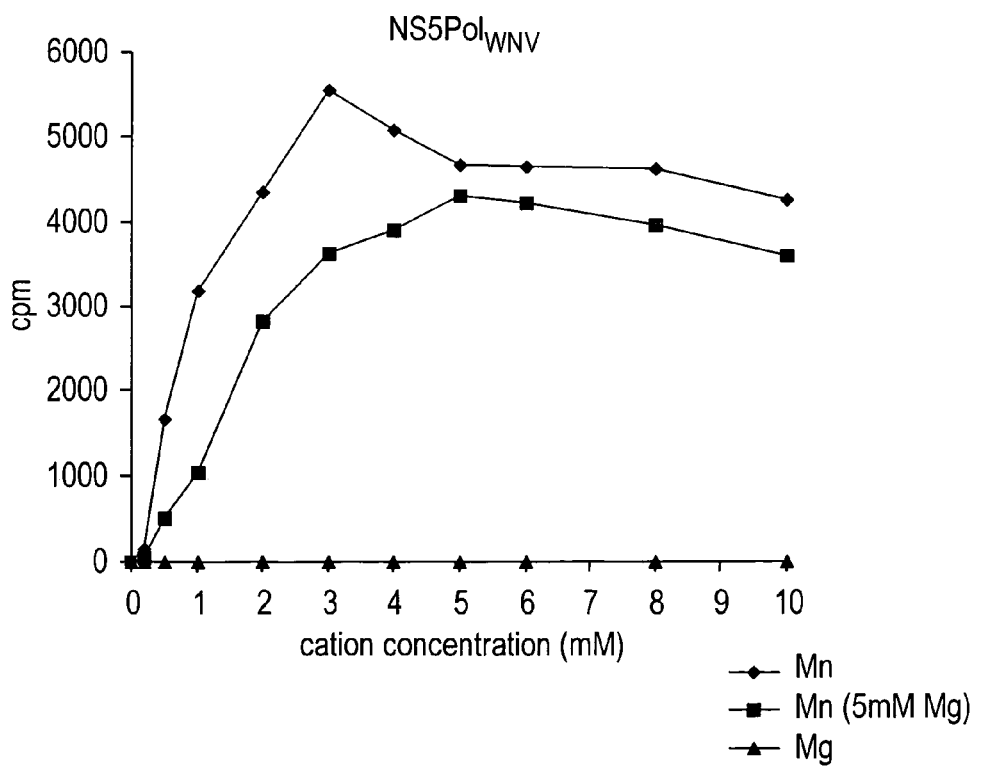

FIG. 6A shows the optimum curve for divalent manganese (Mn) and magnesium (Mg) ions of NS5PolDV on poly(rC). Polymerization on poly(rC) works exclusively in the presence of Mn ions. This is also the case for NS5PolWNV as shown in FIG. 6B. The results set forth in FIG. 6 were obtained pursuant to the following protocol:

A: Tests of NS5PolDV were carried out under standard conditions given in the description set forth above in the experiments related to FIG. 4 at 60 nM enzyme concentration. Influence of Mn2+ was tested either in absence of Mg2+ (Mn) or in presence of 5 mM Mg2+ (Mn (5 mM Mg)). Mg2+ was tested in the absence of Mn2+ (Mg).

B: Test of NS5PolWNV were carried out under the same reaction conditions as for NS5PolDV with the exception of GTP which was used at 100 µM. NS5PolWNV concentration was 400 nM.

Clearly, as seen from FIGS. 6A and 6B, the optimum curves for Mn2+ show that NS5PolWNV tolerates higher Mn2+ concentrations for the polymerization on polyC than NS5PolDV. The apparent Km value for substrate GTP is around 2 to 4-fold higher (130 mM) for NS5PolWNV and NS5PolKV in comparison to NS5PolDV (data not shown). These mechanistic differences between flavivirus polymerases can be studied in detail using well expressed and stable independent NS5Pol domains.

Heteropolymeric Template

NS5PolDV activity was tested on heteropolymeric specific templates comprising 717 nucleotides (225 nt of the 5' and 492 nt of the 3' of the Dengue genome). Specifically, the results are demonstrated in FIG. 7 and were obtained pursuant to the following protocol: Heteropolymeric RNA templates of 717 nt were generated by in vitro transcription using T7 RNA polymerase. The DNA template containing 225 nt of the 5' and 492 nt of the 3' of Dengue genomic RNA was constructed into plasmid pUC18. PCR products with the T7 promoter on the 5' of the positive-sense strand or the 5' of negative-sense strand were generated and used as substrates for in vitro transcription. RNA templates were replicated by NS5PolDV in 50 mM HEPES buffer, pH 8.0 containing 10 mM KCl, 10 mM DTT, 100 nM RNA template, 200 nM NS5PolDV, 500 mM ATP, UTP, GTP, 10 mM CTP and [a-32P]-CTP at 0.1 mCi/ml. Reactions were carried out at 30° C. and stopped by spotting a sample on DEAE 12 filter discs (Whatman) pre-soaked with 50 mM EDTA. Filters were treated as explained above in the experiments related to FIG. 4.

A: Comparison of incorporation on positive-sense and complementary negative-sense minigenome RNA templates. Reactions were carried out as given above except for the use of 500 mM CTP, 50 mM GTP, 0.1 mCi/ml [a-32P]-GTP and 5 mM Mn2+.

B: Divalent-cation optimum curves on positive-sense specific RNA template. Mn2+ was used in the absence of Mg2+ and, likewise, Mg2+ in the absence of Mn2+. Reaction were stopped after 60 min. Incorporation of CMP is given in cpm. The axis on the left corresponds to values obtained in presence of Mn2+ and the axis on the right to values obtained in presence of Mg2+.

This "minigenome" template illustrated in FIG. 7 contains secondary-structure and sequence elements necessary for efficient 7 de novo initiation and replication. Positive-sense and negative-sense RNA was generated by in vitro transcription from PCR products containing the promoter for T7 RNA polymerase in either sense. Specifically, FIG. 7A illustrates that NS5PolDV replicates negative-sense mini-genome RNA with higher efficiency compared to positive-sense RNA. This observation is in accordance with the observation that 10-times more positive-sense genomic RNA is produced in Dengueinfected cells in comparison to negative-sense RNA. Optimum divalent cation concentration (Mn2+ and Mg2+) was determined for replication of the positive-sense template (FIG. 7A). NS5PolDV replicates the template with 20-fold higher efficiency at optimal Mn2+ concentration compared to optimal concentration of Mg2+. The affinity of Mn2+ to active site residues seems to be higher compared to Mg2+ as the optimum concentration is lower.

Selective Inhibition of Dengue Virus Polymerase Activity Using Nucleotide Inhibitors GTP analogs were used on NS5PolDV and NS5PolWNV to demonstrate their capacity to inhibit the NS5 polymerase domain using the homopolymeric template poly(rC). IC50 values were determined using GTP concentrations close to the determinded Km values (10 mM for NS5PolDV and 100 mM for NS5PolWNV). Table 2 shows the determined values of three putative chain terminators (3'-deoxy GTP, 3'-dioxolane 3'-deoxy GTP and 2',3'-dideoxy GTP) and 2'-O-methyl-GTP which is expected to be incorporated into the growing RNA chain, thus acting as a competitive inhibitor.

TABLE 2

IC50 values for selected GTP analogs
Reactions on poly(rC) were done under conditions given in FIG. 4 without a primer. NS5PolDV was used at 60 nM. Incorporation of [3H]-GTP was measured after 15 min. Inhibitors (TriLink Corp.) were tested in the concentration range of 1 nM to 100 mM.

| | IC50 (μM) | |
|---|---|---|
| inhibitor | NS5Pol$_{DV}$ | NS5Pol$_{WNV}$ |
| 3'-deoxy GTP | 0.02 | 0.18 |
| 3'-dioxolane 3'-deoxy GTP | 1.2 | 58 |
| 2',3'-dideoxy GTP | 0.8 | 30 |
| 2'-O-methyl-GTP | 5.6 | 105 |

The capacity of 2'-O-methyl-GTP (10 mM) was compared to inhibit NS5PolDV (dimeric preparation) and full-length NS5DV. Initial velocities were determined on poly(rC) at 10 mM GTP and compared to corresponding values without inhibitor. Initial velocities were determined to be 29.3% for NS5PolDV (dimeric preparation) and 19.3% for NS5DV compared to the proteins without inhibitor. This indicates that the NS5PolDV preparation is less inhibited than the full-length polymerase. Since these inhibition results are not identical, questions related to the putative interference of the capping domain remain when using the full-length polymerase.

It is clear that the removal of the capping domain (methyltransferase domain) which is able to bind GTP and GTP analogs, at the N-terminus of NS5 provides the opportunity to obtain unambiguous data which will show that the present truncated polymerase is the target of these inhibitors. The same applies to non-nucleoside inhibitors.

CONCLUSION

To summarize our results: the polymerase domain of flavivirus NS5

1. is purified with higher yields than full-length NS5. The overall increase in yield of the purified product suitable for HTS assays is >10-fold, facilitating mass production for HTS assays.

2. is much more stable than full-length NS5, as less protein is lost or degraded during the course of purification, giving a cleaner and more homogeneous reagent.

3. is active on homopolymeric and heteropolymeric specific templates. Thus, the capping domain is not necessary for the polymerase activity defined as the capacity to initiate and incorporate nucleotides into RNA. The polymerase domain defined here is a bonafide polymerase useful to conduct drug-screening assays.

4. shows similar affinities for template and substrates as the full-length NS5, and is identical in all points tested in terms of polymerase activity.

5. is unambiguous about being the target of a potential inhibitor. As the capping domain is not present, inhibition of NS5 function by GTP analogues and other molecules cannot be accounted for by inhibition of the capping domain or indirect inhibition of the NS5 polymerase activity by interference of the inhibitor with the capping domain.

6. is a valid polymerase model to conduct inhibitor screening studies with the aim to identify putative inhibitors of flavivirus RNA polymerases.

Baginski S G, Pevear D C, Seipel M, Sun S C, Benetatos C A, Chunduru S K, Rice C M, Collett M S. "Mechanism of action of a pestivirus antiviral compound." Proc Natl Acad Sci USA 2000, 97:7981-6.

Campiani G, Fabbrini M, Morelli E, Nacci V, Greco G, Novellino E, Maga G, Spadari S, Bergamini A, Faggioli E, Uccella I, Bolacchi F, Marini S, Coletta M, Fracasso C, Caccia S. "Non-nucleoside HIV-1 reverse transcriptase inhibitors: synthesis and biological evaluation of novel quinoxalinylethylpyridylthioureas as potent antiviral agents." Antivir Chem Chemother 2000, 11:141-55.

Carroll S S, Tomassini J E, Bosserman M, Getty K, Stahlhut M W, Eldrup A B, Bhat B, Hall D, Simcoe A L, LaFemina R, Rutkowski C A, Wolanski B, Yang Z, Migliaccio G, De Francesco R, Kuo L C, MacCoss M, Olsen D B. "Inhibition of hepatitis C virus RNA replication by 2'-modified nucleoside analogs." J Biol Chem 2003 278:11979-84.

De Clercq E. "Antiviral drugs: current state of the art." J. Clin. Virol. 2001:73-89.

Egloff M P, Benarroch D, Selisko B, Romette J L, Canard B. "An RNA cap (nucleoside-2'-O—)-methyltransferase in the flavivirus RNA polymerase NS5: crystal structure and functional characterization." EMBO J. 2002 21:2757-68.

Khandazhinskaya A L, Shirokova E A, Skoblov Y S, Victorova L S, Goryunova L Y, Beabealashvilli R S, Pronyaeva T R, Fedyuk N V, Zolin V V, Pokrovsky A G, Kukhanova M K. "Carbocyclic dinucleoside polyphosphonates: interaction with HIV reverse transcriptase and antiviral activity." J Med Chem 2002, 45:1284-91.

Lai M M. "RNA polymerase as an antiviral target of hepatitis C virus." Antivir Chem Chemother 2001, 12 Suppl 1:143-7.

Mentel R, Kurek S, Wegner U, Janta-Lipinski M, Gurtler L, Matthes E. "Inhibition of adenovirus DNA polymerase by modified nucleoside triphosphate analogs correlate with their antiviral effects on cellular level." Med Microbiol Immunol (Berl) 2000, 189:91-5.

Mlinaric A, Kreft S, Umek A, Strukelj B. "Screening of selected plant extracts for in vitro inhibitory activity on HIV-1 reverse transcriptase (HIV-1 RT)." Pharmazie 2000, 55:75-7.

Walker M P, Hong Z. "HCV RNA-dependent RNA polymerase as a target for antiviral development." Curr. Opinion Pharmacol. 2002, 2!:1-7.

Wang M, Ng K K, Cherney M M, Chan L, Yannopoulos C G, Bedard J, Morin N, Nguyen-Ba N, Alaoui-Ismaili M H, Bethell R C, James M N. "Non-nucleoside Analogue Inhibitors Bind to an Allosteric Site on HCV NS5B Polymerase." CRYSTAL STRUCTURES AND MECHANISM OF INHIBITION. J Biol Chem 2003 278:9489-95.

Zoulim F. "Therapy of chronic hepatitis B virus infection: inhibition of the viral polymerase and other antiviral strategies." Antiviral Res 1999, 44:1-30.

The invention claimed is:

1. An isolated and purified polypeptide from a flavivirus having polymerase activity, wherein the full-length amino acid sequence of said polypeptide has at least 80% of identity with the SEQ ID NO: 16.

2. The isolated and purified polypeptide of claim 1, wherein the full-length amino acid sequence of said polypeptide has at least 95% of identity with SEQ ID NO:16.

3. An isolated and purified polypeptide from a flavivirus having polymerase activity, wherein said polypeptide is selected from the group consisting of SEQ ID NO: 17, SEQ ID NO: 18, and SEQ ID NO: 19.

4. An isolated and purified polypeptide comprising the polymerase domain of the C-terminus of the NS5 polypeptide of a flavivirus, wherein said polypeptide has having polymerase activity and wherein the full-length amino acid sequence of said polypeptide has at least 80% of identity with the SEQ ID NO: 16.

5. The isolated and purified polypeptide of claim 4, wherein said polypeptide is selected from the group consisting of the polymerase domain of the C-terminus of the NS5 polypeptide of the Dengue 1, Dengue 2 and Dengue 3.

* * * * *

SEQUENCE LISTING

```
<160> NUMBER OF SEQ ID NOS: 15

<210> SEQ ID NO 1
<211> LENGTH: 349
<212> TYPE: PRT
<213> ORGANISM: Flavivirus sp.
<220> FEATURE:
<223> OTHER INFORMATION: Denque 2

<400> SEQUENCE: 1

Gly Thr Gly Asn Ile Gly Glu Thr Leu Gly Glu Lys Trp Lys Ser Arg
  1               5                  10                  15

Leu Asn Ala Leu Gly Lys Ser Glu Phe Gln Ile Tyr Lys Lys Ser Gly
             20                  25                  30

Ile Gln Glu Val Asp Arg Thr Leu Ala Lys Glu Gly Ile Lys Arg Gly
         35                  40                  45

Glu Thr Asp His His Ala Val Ser Arg Gly Ser Ala Lys Leu Arg Trp
     50                  55                  60

Phe Val Glu Arg Asn Met Val Thr Pro Glu Gly Lys Val Val Asp Leu
 65                  70                  75                  80

Gly Cys Gly Arg Gly Gly Trp Ser Tyr Tyr Cys Gly Gly Leu Lys Asn
                 85                  90                  95

Val Arg Glu Val Lys Gly Leu Thr Lys Gly Gly Pro Gly His Glu Glu
            100                 105                 110

Pro Ile Pro Met Ser Thr Tyr Gly Trp Asn Leu Val Arg Leu Gln Ser
        115                 120                 125

Gly Val Asp Val Phe Phe Thr Pro Pro Glu Lys Cys Asp Thr Leu Leu
    130                 135                 140

Cys Asp Ile Gly Glu Ser Ser Pro Asn Pro Thr Val Glu Ala Gly Arg
145                 150                 155                 160

Thr Leu Arg Val Leu Asn Leu Val Glu Asn Trp Leu Asn Asn Asn Thr
                165                 170                 175

Gln Phe Cys Ile Lys Val Leu Asn Pro Tyr Met Pro Ser Val Ile Glu
            180                 185                 190

Lys Met Glu Ala Leu Gln Arg Lys Tyr Gly Gly Ala Leu Val Arg Asn
        195                 200                 205

Pro Leu Ser Arg Asn Ser Thr His Glu Met Tyr Trp Leu Ser Asn Ala
    210                 215                 220
```

```
Ser Gly Asn Ile Val Ser Ser Val Asn Met Ile Ser Arg Met Leu Ile
225                 230                 235                 240

Asn Arg Phe Thr Met Arg His Lys Lys Ala Thr Tyr Glu Pro Asp Val
            245                 250                 255

Asp Leu Gly Ser Gly Thr Arg Asn Ile Gly Ile Glu Ser Glu Ile Pro
                260                 265                 270

Asn Leu Asp Ile Ile Gly Lys Arg Ile Glu Lys Ile Lys Gln Glu His
            275                 280                 285

Glu Thr Ser Trp His Tyr Asp Gln Asp His Pro Tyr Lys Thr Trp Ala
        290                 295                 300

Tyr His Gly Ser Tyr Glu Thr Lys Gln Thr Gly Ser Ala Ser Ser Met
305                 310                 315                 320

Gly Asn Gly Val Val Arg Leu Leu Thr Lys Pro Trp Asp Val Val Pro
                325                 330                 335

Met Val Thr Gln Met Ala Met Thr Asp Thr Thr Pro Phe
                340                 345

<210> SEQ ID NO 2
<211> LENGTH: 348
<212> TYPE: PRT
<213> ORGANISM: Flavivirus sp.
<220> FEATURE Arg Phe Thr Met Thr His Arg Arg Pro Thr Ile Glu Lys Asp Val Asp
                245                 250                 255

Leu Gly Ala Gly Thr Arg His Val Asn Ala Glu Pro Glu Thr Pro Asn
            260                 265                 270

Met Asp Val Ile Gly Glu Arg Ile Lys Arg Ile Lys Glu Glu His Ser
        275                 280                 285

Ser Thr Trp His Tyr Asp Asp Glu Asn Pro Tyr Lys Thr Trp Ala Tyr
    290                 295                 300

His Gly Ser Tyr Glu Val Lys Ala Thr Gly Ser Ala Ser Ser Met Ile
305                 310                 315                 320

Asn Gly Val Val Lys Leu Leu Thr Lys Pro Trp Asp Val Val Pro Met
                325                 330                 335

Val Thr Gln Met Ala Met Thr Asp Thr Thr Pro Phe
                340                 345

<210> SEQ ID NO 3
<211> LENGTH: 348
<212> TYPE: PRT
<213> ORGANISM: Flavivirus sp.
<220> FEATURE:
<223> OTHER INFORMATION: Denque 1

<400> SEQUENCE: 3

Gly Thr Gly Ala Gln Gly Glu Thr Leu Gly Glu Lys Trp Lys Arg Gln
  1               5                  10                  15

Leu Asn Gln Leu Ser Lys Ser Glu Phe Asn Thr Tyr Lys Arg Ser Gly
            20                  25                  30

Ile Met Glu Val Asp Arg Ser Glu Ala Lys Glu Gly Leu Lys Arg Gly
        35                  40                  45

Glu Thr Thr Lys His Ala Val Ser Arg Gly Thr Ala Lys Leu Arg Trp
    50                  55                  60

Phe Val Glu Arg Asn Leu Val Lys Pro Glu Gly Lys Val Ile Asp Leu
65                  70                  75                  80

Gly Cys Gly Arg Gly Gly Trp Ser Tyr Tyr Cys Ala Gly Leu Lys Lys
                85                  90                  95

Val Thr Glu Val Lys Gly Tyr Thr Lys Gly Gly Pro Gly His Glu Glu
            100                 105                 110

Pro Ile Pro Met Ala Thr Tyr Gly Trp Asn Leu Val Lys Leu His Ser
        115                 120                 125

Gly Lys Asp Val Phe Phe Thr Pro Pro Glu Lys Cys Asp Thr Leu Leu
    130                 135                 140

Cys Asp Ile Gly Glu Ser Ser Pro Asn Pro Thr Ile Glu Glu Gly Arg
145                 150                 155                 160

Thr Leu Arg Val Leu Lys Met Val Glu Pro Trp Leu Arg Gly Asn Gln
                165                 170                 175

Phe Cys Ile Lys Ile Leu Asn Pro Tyr Met Pro Ser Val Val Glu Thr
            180                 185                 190

Leu Glu Gln Met Gln Arg Lys His Gly Gly Met Leu Val Arg Asn Pro
        195                 200                 205

Leu Ser Arg Asn Ser Thr His Glu Met Tyr Trp Val Ser Cys Gly Thr
    210                 215                 220

Gly Asn Ile Val Ser Ala Val Asn Met Thr Ser Arg Met Leu Leu Asn
225                 230                 235                 240

Arg Phe Thr Met Ala His Arg Lys Pro Thr Tyr Glu Arg Asp Val Asp
                245                 250                 255

```
Leu Gly Ala Gly Thr Arg His Val Ala Val Glu Pro Glu Val Ala Asn
            260                 265                 270

Leu Asp Ile Ile Gly Gln Arg Ile Glu Asn Ile Lys His Glu His Lys
        275                 280                 285

Ser Thr Trp His Tyr Asp Glu Asp Asn Pro Tyr Lys Thr Trp Ala Tyr
        290                 295                 300

His Gly Ser Tyr Glu Val Lys Pro Ser Gly Ser Ala Ser Ser Met Val
305                 310                 315                 320

Asn Gly Val Val Arg Leu Leu Thr Lys Pro Trp Asp Val Ile Pro Met
                325                 330                 335

Val Thr Gln Ile Ala Met Thr Asp Thr Thr Pro Phe
            340                 345

<210> SEQ ID NO 4
<211> LENGTH: 349
<212> TYPE: PRT
<213> ORGANISM: Flavivirus sp.
<220> FEATURE:
<223> OTHER INFORMATION: Denque 4

<400> SEQUENCE: 4

Gly Thr Gly Thr Thr Gly Glu Thr Leu Gly Glu Lys Trp Lys Arg Gln
1               5                   10                  15

Leu Asn Ser Leu Asp Arg Lys Glu Phe Glu Glu Tyr Lys Arg Ser Gly
            20                  25                  30

Ile Leu Glu Val Asp Arg Thr Glu Ala Lys Ser Ala Leu Lys Asp Gly
        35                  40                  45

Ser Lys Ile Lys His Ala Val Ser Arg Gly Ser Ser Lys Ile Arg Trp
    50                  55                  60

Ile Val Glu Arg Gly Met Val Lys Pro Lys Gly Lys Val Val Asp Leu
65                  70                  75                  80

Gly Cys Gly Arg Gly Gly Trp Ser Tyr Tyr Met Ala Thr Leu Lys Asn
                85                  90                  95

Val Thr Glu Val Lys Gly Tyr Thr Lys Gly Gly Pro Gly His Glu Glu
            100                 105                 110

Pro Ile Pro Met Ala Thr Tyr Gly Trp Asn Leu Val Lys Leu His Ser
        115                 120                 125

Gly Val Asp Val Phe Tyr Lys Pro Thr Glu Gln Val Asp Thr Leu Leu
    130                 135                 140

Cys Asp Ile Gly Glu Ser Ser Ser Asn Pro Thr Ile Glu Glu Gly Arg
145                 150                 155                 160

Thr Leu Arg Val Leu Lys Met Val Glu Pro Trp Leu Ser Ser Lys Pro
                165                 170                 175

Glu Phe Cys Ile Lys Val Leu Asn Pro Tyr Met Pro Thr Val Ile Glu
            180                 185                 190

Glu Leu Glu Lys Leu Gln Arg Lys His Gly Gly Asn Leu Val Arg Cys
        195                 200                 205

Pro Leu Ser Arg Asn Ser Thr His Glu Met Tyr Trp Val Ser Gly Ala
    210                 215                 220

Ser Gly Asn Ile Val Ser Ser Val Asn Thr Thr Ser Lys Met Leu Leu
225                 230                 235                 240

Asn Arg Phe Thr Thr Arg His Arg Lys Pro Thr Tyr Glu Lys Asp Val
                245                 250                 255

Asp Leu Gly Ala Gly Thr Arg Ser Val Ser Thr Glu Thr Glu Lys Pro
            260                 265                 270
```

```
Asp Met Thr Ile Ile Gly Arg Arg Leu Gln Arg Leu Gln Glu Glu His
            275                 280                 285

Lys Glu Thr Trp His Tyr Asp Gln Glu Asn Pro Tyr Arg Thr Trp Ala
        290                 295                 300

Tyr His Gly Ser Tyr Glu Ala Pro Ser Thr Gly Ser Ala Ser Ser Met
305                 310                 315                 320

Val Asn Gly Val Val Lys Leu Leu Thr Lys Pro Trp Asp Val Ile Pro
                325                 330                 335

Met Val Thr Gln Leu Ala Met Thr Asp Thr Thr Pro Phe
            340                 345

<210> SEQ ID NO 5
<211> LENGTH: 351
<212> TYPE: PRT
<213> ORGANISM: Flavivirus sp.
<220> FEATURE:
<223> OTHER INFORMATION: West Nile

<400> SEQUENCE: 5

Gly Gly Ala Lys Gly Arg Thr Leu Gly Glu Val Trp Lys Glu Arg Leu
1               5                   10                  15

Asn Gln Met Thr Lys Glu Glu Phe Thr Arg Tyr Arg Lys Glu Ala Ile
                20                  25                  30

Ile Glu Val Asp Arg Ser Ala Ala Lys His Ala Arg Lys Glu Gly Asn
            35                  40                  45

Val Thr Gly Gly His Ser Val Ser Arg Gly Thr Ala Lys Leu Arg Trp
        50                  55                  60

Leu Val Glu Arg Arg Phe Leu Glu Pro Val Gly Lys Val Ile Asp Leu
65                  70                  75                  80

Gly Cys Gly Arg Gly Gly Trp Cys Tyr Tyr Met Ala Thr Gln Lys Arg
                85                  90                  95

Val Gln Glu Val Arg Gly Tyr Thr Lys Gly Gly Pro Gly His Glu Glu
            100                 105                 110

Pro Gln Leu Val Gln Ser Tyr Gly Trp Asn Ile Val Thr Met Lys Ser
        115                 120                 125

Gly Val Asp Val Phe Tyr Arg Pro Ser Glu Cys Cys Asp Thr Leu Leu
130                 135                 140

Cys Asp Ile Gly Glu Ser Ser Ser Ala Glu Val Glu Glu His Arg
145                 150                 155                 160

Thr Ile Arg Val Leu Glu Met Val Glu Asp Trp Leu His Arg Gly Pro
                165                 170                 175

Arg Glu Phe Cys Val Lys Val Leu Cys Pro Tyr Met Pro Lys Val Ile
            180                 185                 190

Glu Lys Met Glu Leu Leu Gln Arg Arg Tyr Gly Gly Gly Leu Val Arg
        195                 200                 205

Asn Pro Leu Ser Arg Asn Ser Thr His Glu Met Tyr Trp Val Ser Arg
    210                 215                 220

Ala Ser Gly Asn Val Val His Ser Val Asn Met Thr Ser Gln Val Leu
225                 230                 235                 240

Leu Gly Arg Met Glu Lys Arg Thr Trp Lys Gly Pro Gln Tyr Glu Glu
                245                 250                 255

Asp Val Asn Leu Gly Ser Gly Thr Arg Ala Val Gly Lys Pro Leu Leu
            260                 265                 270

Asn Ser Asp Thr Ser Lys Ile Asn Asn Arg Ile Glu Arg Leu Arg Arg
        275                 280                 285
```

Glu Tyr Ser Ser Thr Trp His His Asp Glu Asn His Pro Tyr Arg Thr
    290                 295                 300

Trp Asn Tyr His Gly Ser Tyr Asp Val Lys Pro Thr Gly Ser Ala Ser
305                 310                 315                 320

Ser Leu Val Asn Gly Val Val Arg Leu Leu Ser Lys Pro Trp Asp Thr
                325                 330                 335

Ile Thr Asn Val Thr Thr Met Ala Met Thr Asp Thr Thr Pro Phe
            340                 345                 350

<210> SEQ ID NO 6
<211> LENGTH: 351
<212> TYPE: PRT
<213> ORGANISM: Flavivirus sp.
<220> FEATURE:
<223> OTHER INFORMATION: Kunjin

<400> SEQUENCE: 6

Gly Gly Ala Lys Gly Arg Thr Leu Gly Glu Val Trp Lys Glu Arg Leu
1 5 10 15

Asn Gln Met Thr Lys Glu Glu Phe Ile Arg Tyr Arg Lys Glu Ala Ile
20 25 30

Thr Glu Val Asp Arg Ser Ala Ala Lys His Ala Arg Lys Glu Arg Asn
35 40 45

Ile Thr Gly Gly His Pro Val Ser Arg Gly Thr Ala Lys Leu Arg Trp
50 55 60

Leu Val Glu Arg Arg Phe Leu Glu Pro Val Gly Lys Val Ile Asp Leu
65 70 75 80

Gly Cys Gly Arg Gly Gly Trp Cys Tyr Tyr Met Ala Thr Gln Lys Arg
85 90 95

Val Gln Glu Val Arg Gly Tyr Thr Lys Gly Gly Pro Gly His Glu Glu
100 105 110

Pro Gln Leu Val Gln Ser Tyr Gly Trp Asn Ile Val Thr Met Lys Ser
115 120 125

Gly Val Asp Val Phe Tyr Arg Pro Ser Glu Cys Cys Asp Thr Leu Leu
130 135 140

Cys Asp Ile Gly Glu Ser Ser Ser Ser Ala Glu Val Glu Glu His Arg
145 150 155 160

Thr Leu Arg Val Leu Glu Met Val Glu Asp Trp Leu His Arg Gly Pro
165 170 175

Lys Glu Phe Cys Val Lys Val Leu Cys Pro Tyr Met Pro Lys Val Ile
180 185 190

Glu Lys Met Glu Leu Leu Gln Arg Arg Tyr Gly Gly Gly Leu Val Arg
195 200 205

Asn Pro Leu Ser Arg Asn Ser Thr His Glu Met Tyr Trp Val Ser Arg
210 215 220

Ala Ser Gly Asn Val Val His Ser Val Asn Met Thr Ser Gln Val Leu
225 230 235 240

Leu Gly Arg Met Glu Lys Lys Thr Trp Lys Gly Pro Gln Tyr Glu Glu
245 250 255

Asp Val Asn Leu Gly Ser Gly Thr Arg Ala Val Gly Lys Pro Leu Leu
260 265 270

Asn Ser Asp Thr Ser Lys Ile Lys Asn Arg Ile Glu Arg Leu Arg Arg
275 280 285

Glu Tyr Ser Ser Thr Trp His His Asp Glu Asn His Pro Tyr Arg Thr
290 295 300

```
Trp Asn Tyr His Gly Ser Tyr Glu Val Lys Pro Thr Gly Ser Ala Ser
305                 310                 315                 320

Ser Leu Val Asn Gly Val Val Arg Leu Leu Ser Lys Pro Trp Asp Thr
            325                 330                 335

Ile Thr Asn Val Thr Thr Met Ala Met Thr Asp Thr Thr Pro Phe
        340                 345                 350
```

<210> SEQ ID NO 7
<211> LENGTH: 351
<212> TYPE: PRT
<213> ORGANISM: Flavivirus sp.
<220> FEATURE:
<223> OTHER INFORMATION: Japanese Encephalitis

<400> SEQUENCE: 7

```
Gly Arg Pro Gly Gly Arg Thr Leu Gly Glu Gln Trp Lys Glu Lys Leu
1               5                   10                  15

Asn Ala Met Ser Arg Glu Glu Phe Phe Lys Tyr Arg Arg Glu Ala Ile
            20                  25                  30

Ile Glu Val Asp Arg Thr Glu Ala Arg Arg Ala Arg Arg Glu Asn Asn
        35                  40                  45

Ile Val Gly Gly His Pro Val Ser Arg Gly Ser Ala Lys Leu Arg Trp
    50                  55                  60

Leu Val Glu Lys Gly Phe Val Ser Pro Ile Gly Lys Val Ile Asp Leu
65                  70                  75                  80

Gly Cys Gly Arg Gly Gly Trp Ser Tyr Tyr Ala Ala Thr Leu Lys Lys
                85                  90                  95

Val Gln Glu Val Arg Gly Tyr Thr Lys Gly Gly Ala Gly His Glu Glu
            100                 105                 110

Pro Met Leu Met Gln Ser Tyr Gly Trp Asn Leu Val Ser Leu Lys Ser
        115                 120                 125

Gly Val Asp Val Phe Tyr Lys Pro Ser Glu Pro Ser Asp Thr Leu Phe
    130                 135                 140

Cys Asp Ile Gly Glu Ser Ser Pro Ser Pro Glu Val Glu Glu Gln Arg
145                 150                 155                 160

Thr Leu Arg Val Leu Glu Met Thr Ser Asp Trp Leu His Arg Gly Pro
                165                 170                 175

Arg Glu Phe Cys Ile Lys Val Leu Cys Pro Tyr Met Pro Lys Val Ile
            180                 185                 190

Glu Lys Met Glu Val Leu Gln Arg Arg Phe Gly Gly Gly Leu Val Arg
        195                 200                 205

Leu Pro Leu Ser Arg Asn Ser Asn His Glu Met Tyr Trp Val Ser Gly
    210                 215                 220

Ala Ala Gly Asn Val Val His Ala Val Asn Met Thr Ser Gln Val Leu
225                 230                 235                 240

Leu Gly Arg Met Asp Arg Thr Val Trp Arg Gly Pro Lys Tyr Glu Glu
                245                 250                 255

Asp Val Asn Leu Gly Ser Gly Thr Arg Ala Val Gly Lys Gly Glu Val
            260                 265                 270

His Ser Asn Gln Glu Lys Ile Lys Lys Arg Ile Gln Lys Leu Lys Glu
        275                 280                 285

Glu Phe Ala Thr Thr Trp His Lys Asp Pro Glu His Pro Tyr Arg Thr
    290                 295                 300

Trp Thr Tyr His Gly Ser Tyr Glu Val Lys Ala Thr Gly Ser Ala Ser
305                 310                 315                 320
```

```
Ser Leu Val Asn Gly Val Val Lys Leu Met Ser Lys Pro Trp Asp Ala
                325                 330                 335

Ile Ala Asn Val Thr Thr Met Ala Met Thr Asp Thr Thr Pro Phe
            340                 345                 350

<210> SEQ ID NO 8
<211> LENGTH: 350
<212> TYPE: PRT
<213> ORGANISM: Flavivirus sp.
<220> FEATURE:
<223> OTHER INFORMATION: Yellow Fever

<400> SEQUENCE: 8

Gly Thr Ala Asn Gly Lys Thr Leu Gly Glu Val Trp Lys Arg Glu Leu
 1               5                  10                  15

Asn Leu Leu Asp Lys Gln Gln Phe Glu Leu Tyr Lys Arg Thr Asp Ile
                20                  25                  30

Val Glu Val Asp Arg Asp Thr Ala Arg Arg His Leu Ala Glu Gly Lys
            35                  40                  45

Val Asp Thr Gly Val Ala Val Ser Arg Gly Thr Ala Lys Leu Arg Trp
        50                  55                  60

Phe His Glu Arg Gly Tyr Val Lys Leu Glu Gly Arg Val Ile Asp Leu
 65                  70                  75                  80

Gly Cys Gly Arg Gly Gly Trp Cys Tyr Tyr Ala Ala Ala Gln Lys Glu
                 85                  90                  95

Val Ser Gly Val Lys Gly Phe Thr Leu Gly Arg Asp Gly His Glu Lys
            100                 105                 110

Pro Met Asn Val Gln Ser Leu Gly Trp Asn Ile Ile Thr Phe Lys Asp
        115                 120                 125

Lys Thr Asp Ile His Arg Leu Glu Pro Val Lys Cys Asp Thr Leu Leu
    130                 135                 140

Cys Asp Ile Gly Glu Ser Ser Ser Ser Val Thr Glu Gly Glu Arg
145                 150                 155                 160

Thr Val Arg Val Leu Asp Thr Val Glu Lys Trp Leu Ala Cys Gly Val
                165                 170                 175

Asp Asn Phe Cys Val Lys Val Leu Ala Pro Tyr Met Pro Asp Val Leu
            180                 185                 190

Glu Lys Leu Glu Leu Leu Gln Arg Arg Phe Gly Gly Thr Val Ile Arg
        195                 200                 205

Asn Pro Leu Ser Arg Asn Ser Thr His Glu Met Tyr Tyr Val Ser Gly
    210                 215                 220

Ala Arg Ser Asn Val Thr Phe Thr Val Asn Gln Thr Ser Arg Leu Leu
225                 230                 235                 240

Met Arg Arg Met Arg Arg Pro Thr Gly Lys Val Thr Leu Glu Ala Asp
                245                 250                 255

Val Thr Leu Pro Ile Gly Thr Arg Ser Val Glu Thr Asp Lys Gly Pro
            260                 265                 270

Leu Asp Lys Glu Ala Ile Glu Glu Arg Val Glu Arg Ile Lys Ser Glu
        275                 280                 285

Tyr Met Thr Ser Trp Phe Tyr Asp Asn Asp Asn Pro Tyr Arg Thr Trp
    290                 295                 300

His Tyr Cys Gly Ser Tyr Val Thr Lys Thr Ser Gly Ser Ala Ala Ser
305                 310                 315                 320

Met Val Asn Gly Val Ile Lys Ile Leu Thr Tyr Pro Trp Asp Lys Ile
                325                 330                 335
```

-continued

```
Glu Glu Val Thr Arg Met Ala Met Thr Asp Thr Thr Pro Phe
            340                 345                 350
```

```
<210> SEQ ID NO 9
<211> LENGTH: 350
<212> TYPE: PRT
<213> ORGANISM: Flavivirus sp.
<220> FEATURE:
<223> OTHER INFORMATION: Banzi

<400> SEQUENCE: 9

Gly Gly Ser Ser Ala Leu Thr Tyr Gly Glu Val Trp Lys Arg Gln Leu
  1               5                  10                  15

Asn Leu Leu Gly Lys Gln Glu Phe Met Asn Tyr Lys Val Ser Asp Ile
             20                  25                  30

Leu Glu Val Asp Arg Ser His Ala Arg Glu Val Leu Asn Ser Gly Asn
         35                  40                  45

Asp Ala Val Gly Val Ala Val Ser Arg Gly Ser Ser Lys Leu Asn Trp
     50                  55                  60

Leu Ile Glu Arg Gly Tyr Leu Arg Pro Thr Gly Arg Val Val Asp Leu
 65                  70                  75                  80

Gly Cys Gly Trp Gly Gly Trp Ser Tyr Thr Cys Ala Ala Glu Arg Gln
                 85                  90                  95

Val Thr Ser Val Lys Ala Tyr Thr Leu Gly Lys Glu Gly His Glu Lys
            100                 105                 110

Pro Arg Leu Ile Gln Ser Leu Gly Trp Asn Ile Ile Lys Phe Lys Asp
        115                 120                 125

Lys Ser Asp Ile Thr Arg Met Thr Pro His Ala Ser Asp Thr Leu Leu
    130                 135                 140

Cys Asp Ile Gly Glu Ser Ser Ser Asn Pro Glu Val Glu Lys Glu Arg
145                 150                 155                 160

Thr Leu Arg Val Ile Glu Ala Val Glu Lys Trp Met Ser Pro Thr Thr
                165                 170                 175

Val Ser Phe Cys Phe Lys Val Leu Ala Pro Tyr Lys Pro Asp Val Ile
            180                 185                 190

Glu Ala Leu Glu Arg Phe Gln Leu Lys His Gly Gly Gly Ile Ile Arg
        195                 200                 205

Asn Pro Tyr Ser Arg Asn Ser Thr His Glu Met Tyr Tyr Val Ser Gly
    210                 215                 220

Val Arg Asn Asn Ile Leu His Met Val Asn Ser Thr Ser Arg Met Leu
225                 230                 235                 240

Met Arg Arg Met Ser Arg Pro Ser Gly Arg Ser Thr Val Val Pro Asp
                245                 250                 255

Leu Ile Tyr Pro Thr Gly Thr Arg Ser Val Ala Ser Glu Ala Gly Pro
            260                 265                 270

Leu Asp Leu Glu Lys Val Lys Ala Arg Ile Asn Arg Leu Lys Glu Glu
        275                 280                 285

Gln Glu Ser Thr Trp Phe Val Asp Ser Asp His Pro Tyr Arg Thr Trp
    290                 295                 300

His Tyr His Gly Ser Tyr Val Ala Lys Gln Ser Gly Thr Ala Ala Ser
305                 310                 315                 320

Met Ile Asn Gly Val Val Lys Leu Leu Ser Gly Pro Trp Asp Arg Ile
                325                 330                 335

Glu Glu Val Thr Asn Met Ala Met Thr Asp Thr Thr Pro Phe
            340                 345                 350
```

<210> SEQ ID NO 10
<211> LENGTH: 350
<212> TYPE: PRT
<213> ORGANISM: Flavivirus sp.
<220> FEATURE:
<223> OTHER INFORMATION: Langat

<400> SEQUENCE: 10

Gly Gly Ser Glu Gly Asp Thr Leu Gly Asp Met Trp Lys Ala Arg Leu
 1               5                  10                  15

Asn Ser Cys Thr Lys Glu Glu Phe Phe Ala Tyr Arg Arg Ala Gly Val
            20                  25                  30

Met Glu Thr Asp Arg Glu Lys Ala Arg Glu Leu Leu Lys Arg Gly Glu
        35                  40                  45

Thr Asn Met Gly Leu Ala Val Ser Arg Gly Thr Ser Lys Leu Ala Trp
    50                  55                  60

Met Glu Glu Arg Gly Tyr Val Thr Leu Lys Gly Glu Val Val Asp Leu
65                  70                  75                  80

Gly Cys Gly Arg Gly Gly Trp Ser Tyr Tyr Ala Ala Ser Arg Pro Ala
                85                  90                  95

Val Met Ser Val Arg Ala Tyr Thr Ile Gly Gly Lys Gly His Glu Ser
            100                 105                 110

Pro Arg Met Val Thr Ser Leu Gly Trp Asn Leu Ile Lys Phe Arg Ala
        115                 120                 125

Gly Met Asp Val Phe Ser Met Glu Pro His Arg Ala Asp Ala Ile Leu
    130                 135                 140

Cys Asp Ile Gly Glu Ser Asn Pro Asp Ala Val Val Glu Gly Glu Arg
145                 150                 155                 160

Ser Arg Arg Val Ile Leu Leu Met Glu Gln Trp Lys Asn Arg Asn Pro
                165                 170                 175

Thr Ala Thr Cys Val Phe Lys Val Leu Ala Pro Tyr Arg Pro Glu Val
            180                 185                 190

Ile Glu Ala Leu His Arg Phe Gln Leu Gln Trp Gly Gly Gly Leu Val
        195                 200                 205

Arg Thr Pro Phe Ser Arg Asn Ser Thr His Glu Met Tyr Phe Ser Thr
    210                 215                 220

Ala Ile Thr Gly Asn Ile Val Asn Ser Val Asn Ile Gln Ser Arg Lys
225                 230                 235                 240

Leu Leu Ala Arg Phe Gly Asp Gln Arg Gly Pro Thr Arg Val Pro Glu
                245                 250                 255

Ile Asp Leu Gly Val Gly Thr Arg Cys Val Val Leu Ala Glu Asp Lys
            260                 265                 270

Val Lys Glu Lys Asp Val Met Glu Arg Ile Gln Ala Leu Lys Asp Gln
        275                 280                 285

Tyr Cys Asp Thr Trp His Glu Asp His Glu His Pro Tyr Arg Thr Trp
    290                 295                 300

Gln Tyr Trp Gly Ser Tyr Lys Thr Ala Ala Thr Gly Ser Ser Ala Ser
305                 310                 315                 320

Leu Leu Asn Gly Val Val Lys Leu Leu Ser Trp Pro Trp Asn Ala Arg
                325                 330                 335

Glu Asp Val Val Arg Met Ala Met Thr Asp Thr Thr Ala Phe
            340                 345                 350

<210> SEQ ID NO 11

```
<211> LENGTH: 350
<212> TYPE: PRT
<213> ORGANISM: Flavivirus sp.
<220> FEATURE:
<223> OTHER INFORMATION: Powassan

<400> SEQUENCE: 11

Gly Gly Ala Glu Gly Ser Thr Leu Gly Asp Ile Trp Lys Gln Arg Leu
 1               5                  10                  15

Asn Ser Cys Thr Lys Glu Glu Phe Phe Ala Tyr Arg Arg Thr Gly Val
            20                  25                  30

Met Glu Thr Asn Arg Asp Gln Ala Arg Glu Leu Leu Arg Arg Gly Glu
        35                  40                  45

Thr Asn Met Gly Leu Ala Val Ser Arg Gly Cys Ala Lys Leu Ala Trp
    50                  55                  60

Leu Glu Glu Arg Gly Tyr Ala Thr Leu Lys Gly Glu Val Val Asp Leu
65                  70                  75                  80

Gly Cys Gly Arg Gly Gly Trp Ser Tyr Tyr Ala Ala Ser Arg Pro Ser
                85                  90                  95

Val Met Ala Val Arg Ala Tyr Thr Ile Gly Gly Lys Gly His Glu Ala
            100                 105                 110

Pro Arg Leu Val Thr Ser Leu Gly Trp Asn Leu Ile Lys Phe Arg Ser
        115                 120                 125

Gly Met Asp Val Phe Ser Met Ala Thr Thr Arg Ala Asp Thr Ile Leu
    130                 135                 140

Cys Asp Ile Gly Glu Ser Ser Pro Asp Pro Lys Glu Gly Ala Arg
145                 150                 155                 160

Ser Arg Arg Val Ile Leu Leu Met Glu Gln Trp Lys Ala Arg Asn Pro
                165                 170                 175

Asp Ala Ala Val Phe Lys Val Leu Ala Pro Tyr Arg Pro Glu Val
            180                 185                 190

Leu Glu Ala Leu His Arg Phe Gln Leu Gln Trp Gly Gly Leu Val
        195                 200                 205

Arg Val Pro Phe Ser Arg Asn Ser Thr His Glu Met Tyr Tyr Ser Thr
    210                 215                 220

Ala Val Thr Gly Asn Leu Val Asn Ser Val Asn Val Leu Ser Arg Lys
225                 230                 235                 240

Leu Leu Ala Arg Phe Gly Glu Thr Arg Gly Pro Ile Gln Val Pro Glu
                245                 250                 255

Ile Asp Leu Gly Thr Gly Thr Arg Cys Val Thr Leu Ala Glu Asp Lys
            260                 265                 270

Val Lys Pro Arg Asp Val Ala Glu Arg Ile Gly Ala Leu Arg Glu Gln
        275                 280                 285

Tyr Ser Glu Ser Trp His Glu Asp Lys Glu His Pro Tyr Arg Thr Trp
    290                 295                 300

Gln Tyr Trp Gly Ser Tyr Arg Thr Pro Ala Thr Gly Ser Ala Ala Ser
305                 310                 315                 320

Leu Ile Asn Gly Val Val Lys Leu Leu Ser Trp Pro Trp Asn Ala Arg
                325                 330                 335

Glu Asp Val Thr Arg Met Ala Met Thr Asp Thr Thr Ala Phe
            340                 345                 350

<210> SEQ ID NO 12
<211> LENGTH: 350
<212> TYPE: PRT
<213> ORGANISM: Flavivirus sp.
```

<220> FEATURE:
<223> OTHER INFORMATION: Tick-borne Encephalitis

<400> SEQUENCE: 12

```
Gly Gly Ser Glu Gly Asp Thr Leu Gly Asp Leu Trp Lys Arg Arg Leu
 1               5                  10                  15
Asn Gly Cys Thr Lys Glu Glu Phe Phe Ala Tyr Arg Arg Thr Gly Ile
            20                  25                  30
Leu Glu Thr Glu Arg Asp Lys Ala Arg Glu Leu Leu Arg Arg Gly Glu
        35                  40                  45
Thr Asn Met Gly Leu Ala Val Ser Arg Gly Thr Ala Lys Leu Ala Trp
    50                  55                  60
Leu Glu Glu Arg Gly Tyr Ala Thr Leu Lys Gly Glu Val Val Asp Leu
65                  70                  75                  80
Gly Cys Gly Arg Gly Gly Trp Ser Tyr Tyr Ala Ala Ser Arg Pro Ala
                85                  90                  95
Val Met Ser Val Lys Ala Tyr Thr Ile Gly Gly Lys Gly His Glu Thr
            100                 105                 110
Pro Lys Met Val Thr Ser Leu Gly Trp Asn Leu Ile Lys Phe Arg Ala
        115                 120                 125
Gly Val Asp Val Phe Ser Met Gln Pro His Arg Ala Asp Thr Ile Met
    130                 135                 140
Cys Asp Ile Gly Glu Ser Asn Pro Asp Ala Val Val Glu Gly Glu Arg
145                 150                 155                 160
Thr Arg Lys Val Ile Leu Leu Met Glu Gln Trp Lys Asn Arg Asn Pro
                165                 170                 175
Thr Ala Thr Cys Val Phe Lys Val Leu Ala Pro Tyr Arg Pro Glu Val
            180                 185                 190
Ile Glu Ala Leu His Arg Phe Gln Leu Gln Trp Gly Gly Gly Leu Val
        195                 200                 205
Arg Thr Pro Phe Ser Arg Asn Ser Thr His Glu Met Tyr Tyr Ser Thr
    210                 215                 220
Ala Val Thr Gly Asn Ile Val Asn Ser Val Asn Ile Gln Ser Arg Lys
225                 230                 235                 240
Leu Leu Ala Arg Phe Gly Asp Gln Arg Gly Pro Thr Arg Val Pro Glu
                245                 250                 255
Leu Asp Leu Gly Val Gly Thr Arg Cys Val Val Leu Ala Glu Asp Lys
            260                 265                 270
Val Lys Glu Lys Asp Val Gln Glu Arg Ile Ser Ala Leu Arg Glu Gln
        275                 280                 285
Tyr Gly Glu Thr Trp His Met Asp Arg Glu His Pro Tyr Arg Thr Trp
    290                 295                 300
Gln Tyr Trp Gly Ser Tyr Arg Thr Ala Pro Thr Gly Ser Ala Ala Ser
305                 310                 315                 320
Leu Ile Asn Gly Val Val Lys Leu Leu Ser Trp Pro Trp Asn Ala Arg
                325                 330                 335
Glu Asp Val Val Arg Met Ala Met Thr Asp Thr Thr Ala Phe
            340                 345                 350
```

<210> SEQ ID NO 13
<211> LENGTH: 350
<212> TYPE: PRT
<213> ORGANISM: Flavivirus sp.
<220> FEATURE:
<223> OTHER INFORMATION: LoupingIll

```
<400> SEQUENCE: 13

Gly Gly Ser Asp Gly Asp Thr Leu Gly Asp Leu Trp Lys Arg Arg Leu
 1               5                  10                  15

Asn Asn Cys Thr Lys Glu Glu Phe Phe Val Tyr Arg Arg Thr Gly Ile
             20                  25                  30

Leu Glu Thr Glu Arg Asp Lys Ala Arg Glu Leu Leu Arg Arg Gly Glu
         35                  40                  45

Thr Asn Met Gly Leu Ala Val Ser Arg Gly Thr Ala Lys Leu Ala Trp
     50                  55                  60

Leu Glu Glu Arg Gly Tyr Arg Thr Leu Lys Gly Glu Val Val Asp Leu
 65                  70                  75                  80

Gly Cys Gly Arg Gly Gly Trp Ser Tyr Tyr Ala Ala Ser Arg Pro Ala
                 85                  90                  95

Val Met Ser Val Arg Ala Tyr Thr Ile Gly Gly Arg Gly His Glu Val
                100                 105                 110

Pro Lys Met Val Thr Ser Leu Gly Trp Asn Leu Ile Arg Phe Arg Ser
                115                 120                 125

Gly Met Asp Val Phe Ser Met Gln Pro His Arg Ala Asp Thr Ile Met
        130                 135                 140

Cys Asp Ile Gly Glu Ser Asn Pro Asp Ala Ala Val Glu Gly Glu Arg
145                 150                 155                 160

Thr Arg Lys Val Ile Ser Leu Met Glu Gln Trp Lys Ile Arg Asn Pro
                165                 170                 175

Ala Ala Ala Cys Val Phe Lys Val Leu Ala Pro Tyr Arg Pro Glu Val
                180                 185                 190

Ile Glu Ala Leu His Arg Phe Gln Leu Gln Trp Gly Gly Gly Leu Val
                195                 200                 205

Arg Thr Pro Phe Ser Arg Asn Ser Thr His Glu Met Tyr Tyr Ser Thr
        210                 215                 220

Ala Val Thr Gly Asn Ile Val Asn Ser Val Asn Ile Gln Ser Arg Lys
225                 230                 235                 240

Leu Leu Ala Arg Phe Gly Asp Gln Arg Gly Pro Thr Lys Val Pro Glu
                245                 250                 255

Ala Asp Leu Gly Val Gly Thr Arg Cys Val Val Leu Ala Glu Asp Lys
                260                 265                 270

Val Lys Glu Gln Asp Val Gln Glu Arg Ile Arg Ala Leu Arg Lys Gln
                275                 280                 285

Tyr Ser Glu Thr Trp His Met Asp Glu Glu His Pro Tyr Arg Thr Trp
        290                 295                 300

Gln Tyr Trp Gly Thr Ser Arg Thr Ala Pro Thr Gly Ser Ala Ala Ser
305                 310                 315                 320

Leu Ile Asn Gly Val Val Lys Leu Leu Ser Trp Pro Trp Asn Ala Arg
                325                 330                 335

Glu Asp Val Val Arg Met Ala Met Thr Asp Thr Thr Ala Phe
                340                 345                 350

<210> SEQ ID NO 14
<211> LENGTH: 352
<212> TYPE: PRT
<213> ORGANISM: Flavivirus sp.
<220> FEATURE:
<223> OTHER INFORMATION: Modoc

<400> SEQUENCE: 14

Arg Gly Ile Cys Ser Ser Ala Pro Thr Leu Gly Glu Ile Trp Lys Arg
```

```
            1               5              10              15
Lys Leu Asn Gln Leu Asp Ala Lys Glu Phe Met Ala Tyr Arg Arg Arg
                 20                  25                  30
Phe Val Glu Val Asp Arg Asn Glu Ala Arg Glu Ala Leu Ala Lys
             35                  40                  45
Gly Lys Thr Asn Thr Gly His Ala Val Ser Arg Gly Thr Ala Lys Leu
             50                  55                  60
Ala Trp Ile Asp Glu Arg Gly Gly Val Glu Leu Lys Gly Ser Val Val
65                  70                  75                  80
Asp Leu Gly Cys Gly Arg Gly Gly Trp Ser Tyr Tyr Ala Ala Ser Gln
                 85                  90                  95
Pro Asn Val Arg Glu Val Lys Ala Tyr Thr Leu Gly Thr Ser Gly His
                100                 105                 110
Glu Lys Pro Arg Leu Val Glu Thr Phe Gly Trp Asn Leu Ile Thr Phe
            115                 120                 125
Lys Ser Lys Val Asp Val Arg Lys Met Glu Pro Phe Gln Ala Asp Thr
            130                 135                 140
Val Leu Cys Asp Ile Gly Glu Ser Asn Pro Thr Ala Ala Val Glu Ala
145                 150                 155                 160
Ser Arg Thr Leu Thr Val Leu Asn Val Ile Ser Arg Trp Leu Glu Tyr
                165                 170                 175
Asn Gln Gly Cys Gly Phe Cys Val Lys Val Leu Asn Pro Tyr Ser Cys
                180                 185                 190
Asp Val Leu Glu Ala Leu Met Lys Met Gln Arg Arg Phe Gly Gly Gly
            195                 200                 205
Leu Ile Arg Val Pro Leu Ser Arg Asn Ser Thr His Glu Met Tyr Phe
            210                 215                 220
Val Ser Gly Ile Lys Asn Asn Ile Met Gly Asn Val Thr Ala Val Ser
225                 230                 235                 240
Arg Gln Leu Leu Lys Arg Met Glu Gln Gly Gly Glu Arg Val Val
                245                 250                 255
Pro Asp Tyr Lys Phe Ser Thr Gly Thr Arg Ser Asn Leu Thr Gln Lys
            260                 265                 270
Ile Glu Val Pro Glu Glu Val Gln Met Arg Val Asp Lys Ile Lys
            275                 280                 285
Ala Glu Lys Ser Gly Thr Trp Cys Phe Asp Ser Asn His Pro Tyr Arg
            290                 295                 300
Thr Trp Asn Tyr His Gly Ser Tyr Arg Val Arg Asp Val Gly Thr Arg
305                 310                 315                 320
Ala Ser Ala Val Asn His Val Val Lys Leu Leu Ser Trp Pro Trp Gly
                325                 330                 335
Lys Met Glu Lys Val Leu Ala Met Ser Met Thr Asp Thr Thr Ala Phe
            340                 345                 350

<210> SEQ ID NO 15
<211> LENGTH: 352
<212> TYPE: PRT
<213> ORGANISM: Flavivirus sp.
<220> FEATURE:
<223> OTHER INFORMATION: RioBravo

<400> SEQUENCE: 15

Arg Gly Val Ser Ser Ser Tyr Ile Thr Tyr Gly Glu Gln Trp Lys Arg
1               5                  10                  15

Glu Leu Asn Lys Leu Asn Ala Gln Ala Phe Phe Leu Tyr Lys

-continued

```
                    20                  25                  30
Leu Val His Glu Ile Asp Arg Ala Glu Ala Val Ser Asn Leu Ser Lys
            35                  40                  45

Gly Arg Thr Asn Thr Gly His Ala Val Ser Arg Gly Thr Ser Lys Leu
        50                  55                  60

Ala Trp Met His Glu Arg Gly Tyr Val Pro Leu Lys Gly Val Val Val
 65                  70                  75                  80

Asp Leu Gly Ser Gly Arg Gly Gly Trp Ser Tyr Tyr Ala Ala Ala Gln
                85                  90                  95

Glu Arg Val Arg Lys Val Asn Ala Tyr Thr Leu Ala Thr Thr Lys Gly
               100                 105                 110

His Glu Gln Pro Arg Leu Val Gln Ser Tyr Gly Trp Asn Leu Val Thr
             115                 120                 125

Phe Lys Lys Ala Asp Val Arg Thr Ile Glu Pro Tyr Pro Val Asp Thr
         130                 135                 140

Leu Leu Cys Asp Ile Gly Glu Ser Ser Ser Ser Ser Ile Glu Ala
145                 150                 155                 160

Lys Arg Thr Leu Gln Ile Met Asp Val Val Gly Lys Trp Leu Glu Ile
                165                 170                 175

Ser Pro Gly Ala Ser Phe Cys Ile Lys Ile Leu Cys Pro Tyr Asn Pro
             180                 185                 190

Glu Val Ile Glu His Leu Ser Arg Trp Gln His Gln Phe Gly Gly Gly
         195                 200                 205

Leu Val Arg Val Pro His Ser Arg Asn Ser Thr His Glu Met Tyr Phe
    210                 215                 220

Val Ser Gly Gly Gly Asn Leu Met Ser Ser Ile Thr Ala Val Thr
225                 230                 235                 240

Thr Gln Leu Met Arg Arg Phe Thr Leu Glu Ala Gly Pro Arg His Val
                245                 250                 255

Phe Asp Ile Asn Leu Gly Val Gly Thr Arg Ser Asn Leu Met Glu Lys
             260                 265                 270

Ser Glu Ala Asp Lys Ser Leu Ile Ala Asp Arg Ile Thr Ile Ile Gln
         275                 280                 285

Asn Glu Asn Lys Ala Ser Trp His Gln Asp Pro Asn Gln Pro Tyr Arg
    290                 295                 300

Thr Trp Thr Tyr His Gly Ser Tyr Ser Ile Arg Asp Val Gly Thr Ser
305                 310                 315                 320

Ala Ser Ala Pro Asn His Val Val Lys Leu Leu Ala Trp Pro Trp Leu
                325                 330                 335

Lys Ile Glu Lys Val Val Leu Met Ala Met Thr Asp Thr Thr Ala Phe
             340                 345                 350
```